(12) United States Patent
Warthoe

(10) Patent No.: US 6,261,770 B1
(45) Date of Patent: Jul. 17, 2001

(54) METHOD TO CLONE MRNAS

(75) Inventor: Peter Rolf Warthoe, Copenhagen (DK)

(73) Assignee: Display Systems Biotech ApS, Copenhagen (DK)

( * ) Notice: Subject to any disclaimer, the term of this patent is extended or adjusted under 35 U.S.C. 154(b) by 0 days.

(21) Appl. No.: 09/068,860

(22) Filed: May 19, 1998

(30) Foreign Application Priority Data

May 13, 1997 (DK) .................................................. 0547/97
Mar. 27, 1998 (DK) .................................................. 0432/98

(51) Int. Cl.[7] ............................ C12P 1/168; C12P 19/34; C07H 21/00
(52) U.S. Cl. ......................... 435/6; 435/91.2; 435/91.52; 536/25.32
(58) Field of Search ........................ 435/6, 91.2, 91.52; 536/25.32

(56) References Cited

U.S. PATENT DOCUMENTS

| 5,244,797 | 9/1993 | Kotewicz et al. | 435/194 |
| 5,262,311 | * 11/1993 | Pardes et al. | 435/91.6 |

(List continued on next page.)

FOREIGN PATENT DOCUMENTS

| 0743367 A2 | 11/1996 | (EP) | C12Q/1/68 |
| WO 93/18176 | 9/1993 | (WO) | C12P/19/34 |

(List continued on next page.)

OTHER PUBLICATIONS

R. Williams, "The preparation and screening of a cDNA clone bank", Academic Press, Inc.(1981), pp. 1–59.

(List continued on next page.)

*Primary Examiner*—W. Gary Jones
*Assistant Examiner*—Joyce Tung
(74) *Attorney, Agent, or Firm*—Thomas J. Kowalski; Frommer Lawrence & Haug LLP

(57) ABSTRACT

Disclosed and claimed is a method for preparing a normalized sub-divided library of amplified cDNA fragments from the coding region of mRNAs contained in a sample. The method includes the steps of: a) subjecting the mRNA population to reverse transcription using at least one cDNA primer, thereby obtaining first strand cDNA fragments, b) synthesizing second strand cDNA complementary to the first strand cDNA fragments by use of the first strand DNA fragments as templates, thereby obtaining double stranded cDNA fragments, c) digesting the double stranded cDNA fragments with at least one restriction endonuclease, the endonuclease leaving protruding sticky ends of similar size at the termini of the DNA after digestion, thereby obtaining cleaved cDNA fragments, d) adding at least two adapter fragments containing known sequences to the cleaved cDNA fragments obtained in step c), the at least two adapter fragments being able to bind specifically to the sticky ends of the double stranded cDNA produced in step c), the one adapter fragment being able to anneal to the primer having formula I in step f), the second adapter fragment being a termination fragment introducing a block against DNA polymerization in the 5'→3' direction setting out from said termination fragment and the termination fragment being unable to anneal to any primer of the at least two primer sets in step f) during the molecular amplification procedure, the at least two adapter fragments being ligated to the cleaved cDNA fragments obtained in step c) so as to obtain ligated cDNA fragments, e) sub-dividing the ligated cDNA fragments obtained in step d) into $4^{n1}$ pools where $1 \leq n1 \leq 4$, and f) subjecting each pool of ligated cDNA fragments obtained in step e) to a molecular amplification procedure so as to obtain amplified cDNA fragments, wherein is used, for an adapter fragment used in step d), a set of amplification primers having the general formula I $$5'\text{-Com-}N_{n1}\text{-}3' \qquad \qquad I$$

wherein Com is a sequence complementary to at least the 5'-end of an adapter fragment which is ligated to the 3'-end of a cleaved cDNA fragment, N is A, G, T, or C, the one primer having the general formula I where n1=0, and the second primer having the general formula I where $1 \leq n1 \leq 4$, the second primer being capable of priming amplification of any nucleotide sequence ligated in its 3'-end to the adapter fragment complementary in its 5'-end to Com.

23 Claims, 12 Drawing Sheets

U.S. PATENT DOCUMENTS

| | | | |
|---|---|---|---|
| 5,310,652 | 5/1994 | Gelfand et al. | 435/6 |
| 5,405,776 | 4/1995 | Kotewicz et al. | 435/252.33 |
| 5,459,037 | 10/1995 | Sutcliffe et al. | 435/6 |
| 5,593,840 * | 1/1997 | Bhatnagar et al. | 435/6 |
| 5,599,672 | 2/1997 | Liang et al. | 435/6 |
| 5,665,547 | 9/1997 | Pardee et al. | 435/6 |
| 5,668,005 | 9/1997 | Kotewicz et al. | 435/184 |
| 5,712,126 | 1/1998 | Weissman et al. | 435/91.2 |
| 5,807,680 | 9/1998 | Sutcliffe et al. | 435/6 |
| 5,814,445 | 9/1998 | Belyavsky et al. | 435/6 |
| 5,876,932 | 3/1999 | Fischer | 435/6 |

FOREIGN PATENT DOCUMENTS

| | | | |
|---|---|---|---|
| WO 93/24655 | 12/1993 | (WO) | C12Q/1/68 |
| WO 95/08647 | 3/1995 | (WO) | C12Q/1/68 |
| WO 95/33760 | 12/1995 | (WO) | C07H/21/04 |
| WO 95/13369 | 5/1996 | (WO) | C12Q/15/11 |
| WO 97/05286 | 2/1997 | (WO) | C12Q/1/68 |
| WO 95/29211 | 8/1997 | (WO) | C12Q/1/68 |
| WO 97/29211 | 8/1997 | (WO) | C12Q/1/68 |

OTHER PUBLICATIONS

Bauer D. et al., "Differential Display Reserse Transcription PCR", BIOTEC (1994), pp. 32, 34/35.

"Construction And Analysis of cDNA Libraries" Molecular Cloning, Second Edition, J. Sambrook, E.F. Fritsch And T. Maniatis (1989), pp. 8.11–8.17.

Patanjali S.R. et al., "Construction Of A Uniform–Abundance (Normalized) CDNA Library" Proceedings Of The National Academy Of Sciences Of USA (1991), vol. 88, No. 5, pp. 1943–1947.

Thomas P. St. John et al., "Isolation of Galactose–Inducible DNA Sequences From *Saccharomyces cerevisiae* by Differential Plaque Filter Hybridization", Department of Biochemistry, Stanformd University School of Medicine (1979), vol. 16, 443–452.

J. Lynn Zimmerman et al., "Evidence For A Complex Class Of Nonadenylated mRNA In Drosophilia", Department of Development and Cell Biology and Molecular Biology and Biochemistry (1980) Genetics: 95:673–691.

Peng Liang et al., "Differential Display of Eukaryotic Messenger RNA by Means of the Polymerase Chain Reaction", Science (1992), vol. 257; pp. 967–971.

John Welsh et al., "Arbitrarily primed PCR fingerprinting of RNA", Oxford University Press (1992), Nucleic Acids Research, vol. 20, No. 19, pp. 4965–4970.

David Bauer et al., Identification of differentially expressed mRNA species by an improved display technique (DDRT–PCR), Oxford University Press (1993), vol. 21, No. 18, pp. 4272–4280.

Peter Warthoe et al., "Detection and Identification of Expressed Genes by Differential Display", PCR Primer a Laboratory Manual, pp. 421–438.

Peng Liang et al., "Analysis of Altered Gene Expression by Differential Display" Oncogene Technique, vol. 254 of Methods In Engymology.

Mikkel Rohde et al., "The retinoblastoma protein modulates expression of genes coding for diverse classes of proteins including components of the extracellular matrix" Oncogene (1996) pp. 2393–2401.

Vered Ribon et al., "Nerve Growth Factor Stimluates the Tyrosine Phosphorylation of Endogenous Crk–II and Augments Its Association with $p130^{Cas}$ in PC–12 Cells", The Journal of Biological Chemistry (1996), vol. 271, No. 13, pp. 7375–7380.

Yatindra Prashar et al., "Analysis of differential gene expression by display of 3' end restriction fragments of cDNAs", Proc. Natl. Acad. Sci USA (1996), vol. 93, pp. 659–666.

Charles et al., "Cloning, characterization, and expression of cDNA encoding an inducible nitric oxide synthase from the human chondrocyte" *Nature* 90:11419–11423 (Dec. 1993).

Chartrain et al., "Molecular Cloning, Structure, and Chromosomal Localization of the Human Inducible Nitric Oxide Synthase Gene" *J. Biol. Chem.* 269(9):6765–6772 (1994).

DeVera et al., "Transcriptional regulation of human inducible nitric oxide synthase (NOS2) gene by cytokines: Initial analysis of the human NOS2 promoter" *Proc. Natl. Acad. Sci. USA* 93:1054–1059 (Feb. 1996).

Geller et al., "Molecular cloning and expression of inducible nitric oxide synthase from human hepatocytes" *Proc. Natl. Acad. Sci. USA* 90:2491–3495 (Apr. 1993).

Kamijo et al., "Requirement for Transcription Factor IRF–1 in No Synthase Induction in Macrophages" *Science* 263:1612–1615 (Mar. 18, 1994).

Kleinert et al., "Glucocorticoids Inhibit the Induction of Nitric Oxide Synthase II by Down–regulating Cytokine–Induced Activity of Transcription Factor Nuclear Factor–κB" *Molecular Pharmacology* 49:15–21 (1996).

Lowenstein et al., "Macrophage nitric oxide synthase gene: Two upstream regions mediate induction by interferon γ and lipopolysaccharide" *Proc. Natl. Acad. Sci. USA* 90:9730–9734 (Oct. 1993).

MacMicking et al., "Altered Responses to Bacterial Infection and Endotoxic Shock in Mice Lacking Inducible Nitric Oxide Synthase" *Cell* 81:641–650 (May 19, 1995).

Martin et al., "Role of Interferon Regulatory Factor 1 in Induction of Nitric Oxide Synthase" *J. Exp. Med.* 180:977–984 (Sep. 1994).

Nunokawa et al. "Cloning of Inducible nitric oxide synthase in rat vascular smooth muscle cells" *Biochem. Biophys. Res. Commun.* 191:89–94 (Feb. 26, 1993).

Nunokawa et al. "Promoter analysis of human inducible nitric oxide synthase gene associated with cardiovascular homeostasis" *Biochem. Biophys. Res. Commun.* 200:802–807 (Apr. 29, 1994).

Nunokawa et al. "Human inducible nitric oxide synthase gene is transcriptionally regulated by nuclear factor–κB dependent mechanism" *Biochem. Biophys. Res. Commun.* 223:347–352 (1996).

Sherman et al., "Purification and cDNA Sequence of an Inducible Nitric Oxide Synthase from a Human Tumor Cell Line" *Biochemistry* 32:11600–11605 (1993).

Vodovotz et al., "Mechanisms of Suppression of Macrophage Nitric Oxide Release by Transforming Growth Factor β" *J. Exp. Med.* 178:605–613 (Aug. 1993).

Wei et al., "Altered immune responses in mice lacking inducible nitric oxide synthase" *Nature* 375:408–411 (Jun. 1995).

Xie et al., "Promoter of the Mouse Gene Encoding Calcium-independent Nitric Oxide Synthase Confers Inducibility by Interferon γ and Bacterial Lipopolysaccharide" *J. Exp. Med.* 177:1779–1784 (Jun. 1993).

Xie et al., "Role of Transcription Factor NF–κB/Rel in Induction of Nitric Oxide Synthase" *J. Biol. Chem.* 269(7):4705–4708 (1994).

Straus et al. Genomic subtraction for cloning DNA corresponding to deletion mutations, Proc. Natl. Acad. Sci. USA, vol. 87, p. 1889–1893, 1990.*

* cited by examiner

Fig. 1 Basis of DODET
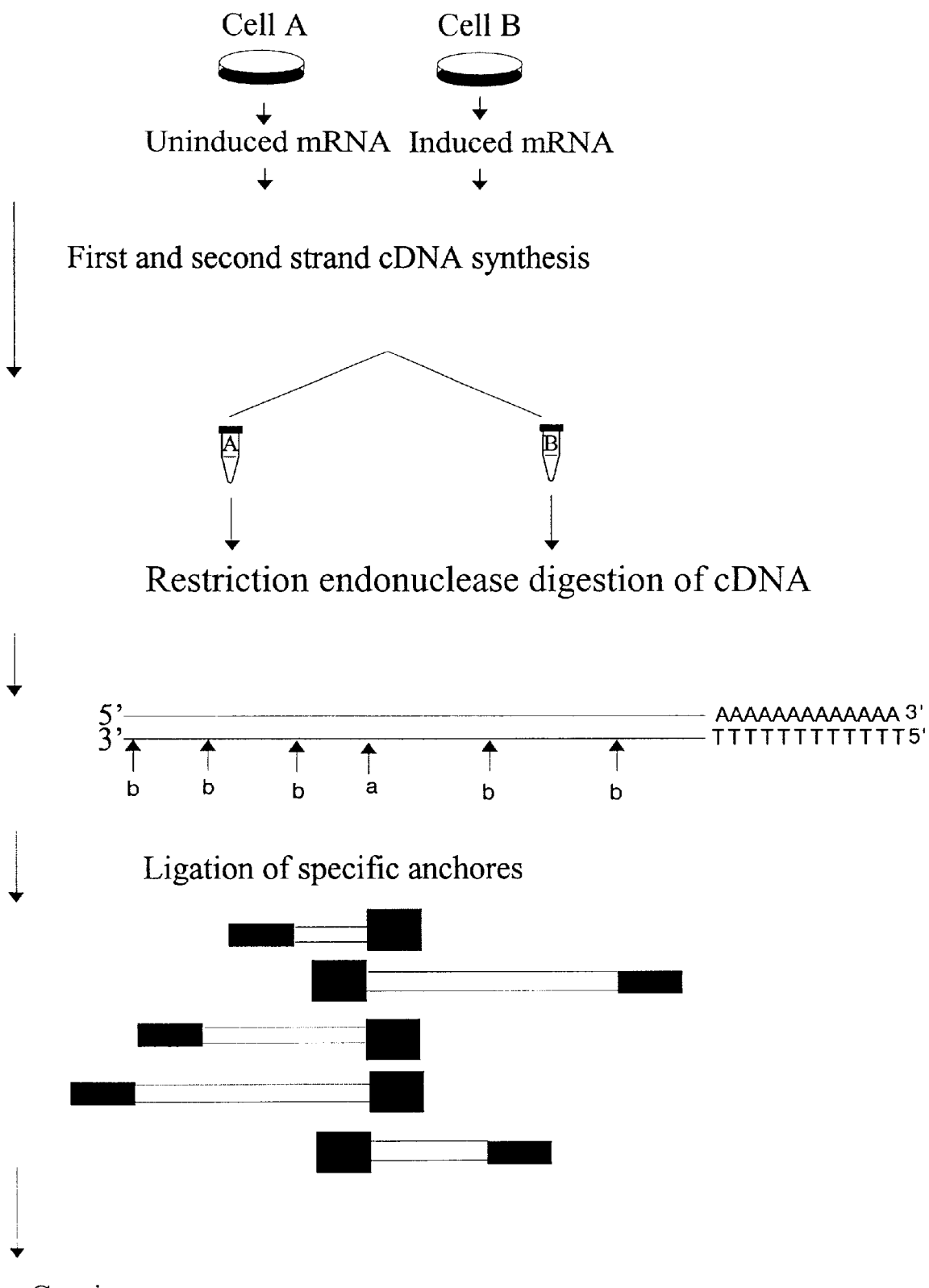
Continue next page

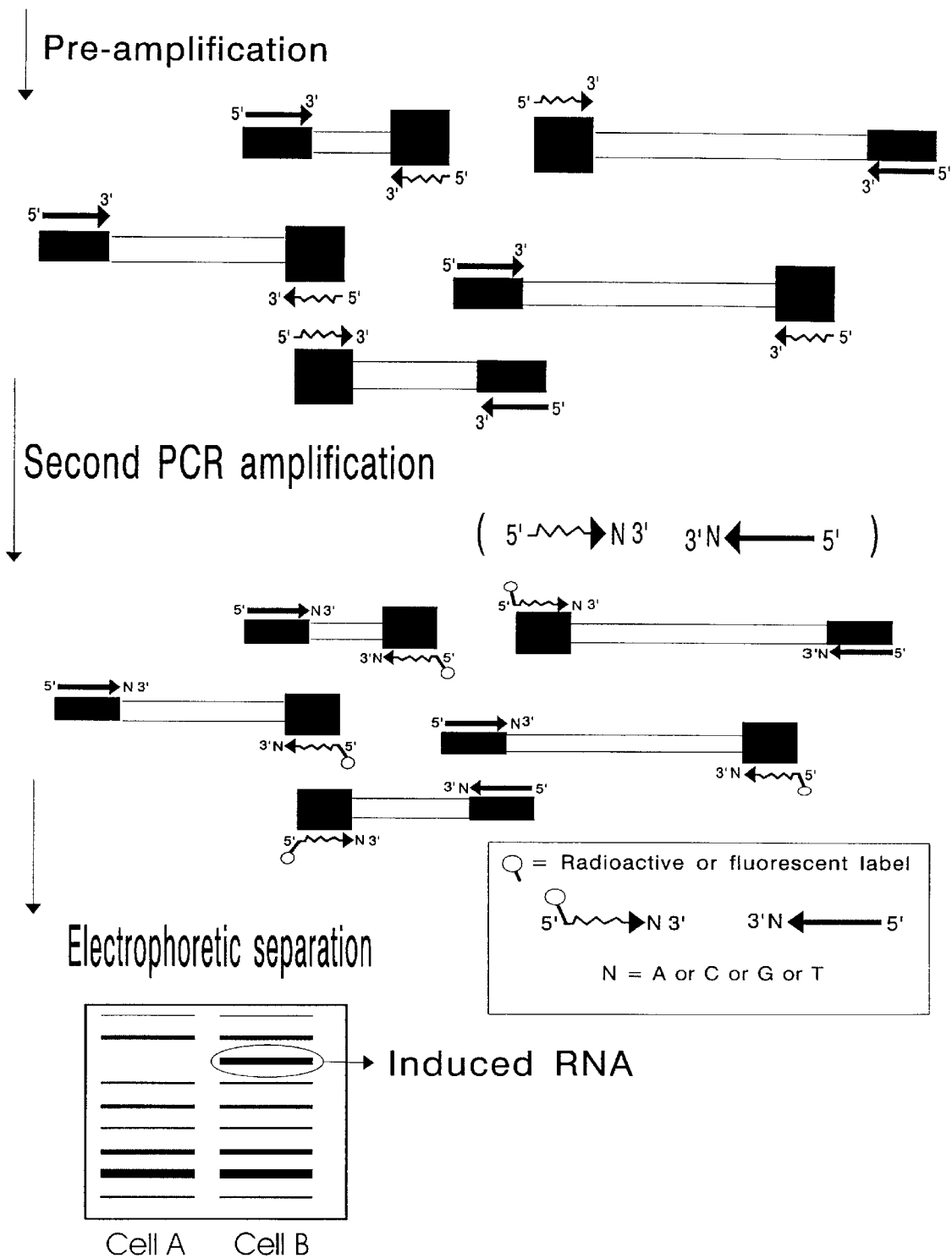

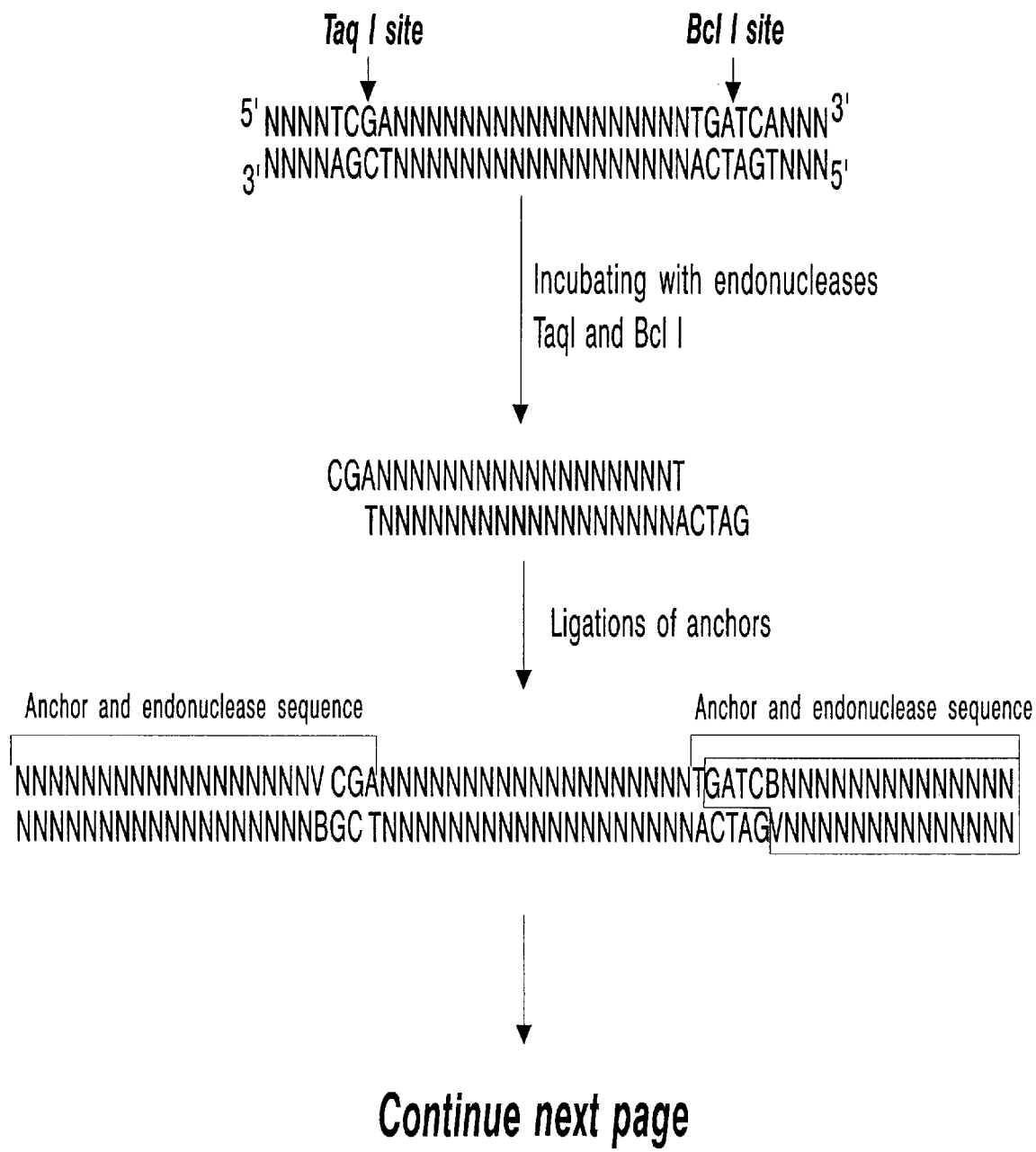

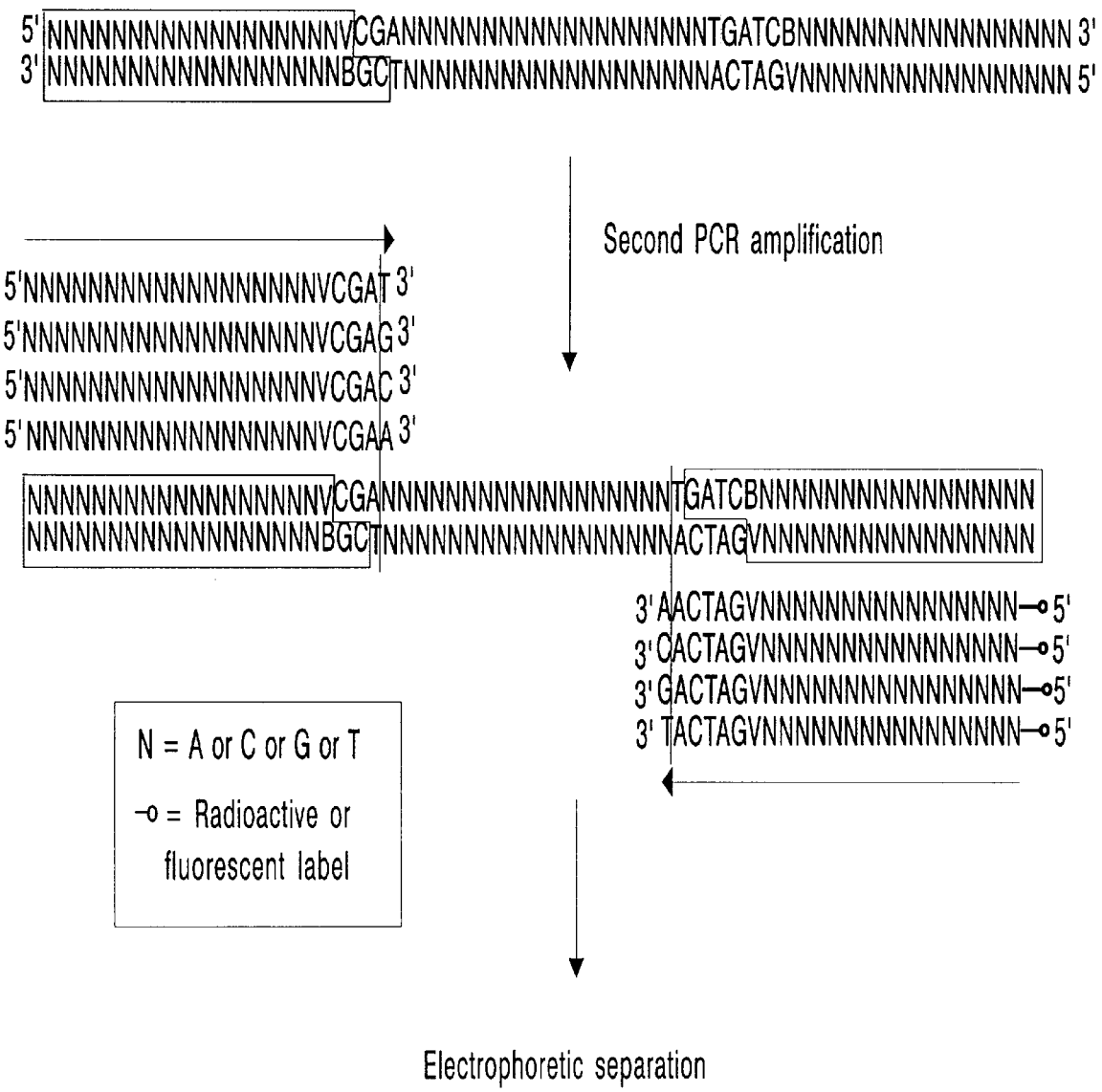
Fig. 2 Anchor and PCR primer design (continue)

a b c d a b c d a b c d a b c d displayARRAY principle

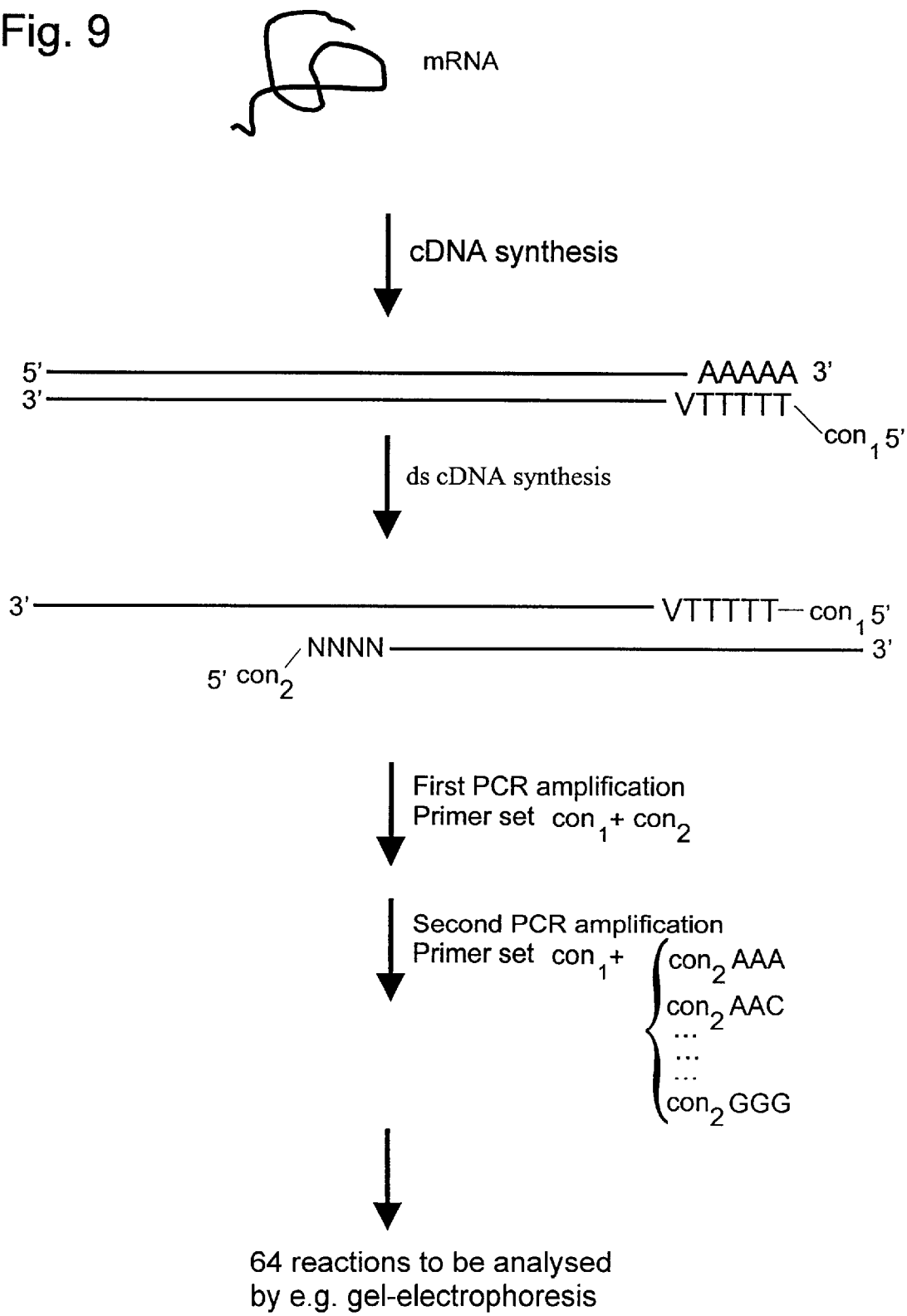

METHOD TO CLONE MRNAS

BACKGROUND OF THE INVENTION

The human body is comprised primarily of specialised cells performing different physiological functions organised into organs and tissues. All human cells contain DNA, arranged in a series of sub-units known as genes. It is estimated that there are approximately 100,000 genes in the human genome. Genes are the blueprints for proteins. Proteins may perform a wide variety of biological functions, for example messengers, catalysts and sensors. Such compounds are responsible for managing most of the physiological and biochemical functions in humans and all other living organisms. Over the last few decades, there has been a growing recognition that many major diseases have a genetic basis. It is now well established that genes play an important role in cancer, cardiovascular diseases, psychiatric disorders, obesity, and metabolic diseases. Significant resources are being focused on genomic research based on the notion that the nucleotide sequences of a particular gene and its predicted protein product will lead to an understanding of its function in healthy and malfunctioning cells or tissues. This understanding is expected, in turn, to lead to therapeutic and diagnostic approaches, focused on molecular targets associated with the gene and the protein it expresses. The first step on the way to the development of such applications is to identify the genes specifically involved in the different categories of diseases. Application of this knowledge can produce new and valuable markers, identifying regions producing major diseases to be used for diagnostic and therapeutic benefit.

Faced with the high complexity of the human genome, many approaches are being used to unravel the connection between primary gene structure and function. One well publicised approach is embodied in the Human Genome Mapping Project, where the sequence of all the individual genes in the entire human genome is painstakingly being determined. At the present, however, little information can be directly retrieved on the function of the identified genes and still less about temporal and spatial expression patterns of the developing or mature organism. Other approaches, such as random cDNA sequencing, involve the sequence determination of all genes expressed in a certain tissue, or developmental stage, of an organism. Like a number of other strategies, this is time consuming and prone to numerous problems.

Although the flood of data from large scale sequencing programmes is of enormous benefit to the scientific community, one of the major problems faced by such "shotgun" approaches is the lack of specific information that can be retrieved without significantly more work on the biology of each of the individual genes.

Several other approaches have been taken by molecular biologists to obtain more specific information on the genetic background of particular biological processes. Such approaches rely on a common concept. One gene, or a subset of genes, is switched on, initiating the healthy, pathological, or developmental status of an organ or cell type.

In a large number of experimental systems the isolation of genes, on the basis of their differential expression, has been applied successfully. Differential screening and subtractive hybridisation of cDNA libraries have become well established, cf. Zimmerman et al. (1980) and Davis et al. (1979). Differential library screening works well in practice for genes that are highly expressed, but mRNAs of low abundance are difficult to isolate. Subtractive hybridisation provides a more sensitive screening, but requires large amounts of RNA. More recently RNA fingerprinting methods (often referred to as differential display or DD/RT PCR) have been added to these tools, offering attractive new features for isolating genes. RNA fingerprinting methods are PCR based and therefore do not require large amounts of RNA for experiments. In addition to this, RNA fingerprinting methods allow a large number of RNA pools to be screened for specific mRNAs simultaneously. Investigation of a wide range of pathogenic developmental stages and their controls would be possible. To date, two methods of RNA fingerprinting have proven useful for isolating genes. In 1992 Liang et al. published a protocol (U.S. Pat. No. 5,262,311), soon after a protocol from Welsh et al. (1992) was presented. Both methods begin with cDNA synthesis from RNA using at least one arbitrary primer for the initiation of first and second strand synthesis.

Welsh et al. (1992) designed a protocol in which the same arbitrary 20-mer oligo is used for first and second strand synthesis. Using arbitrary primers only a subset of the mRNAs are transcribed to cDNA. The cDNA pools are then used for a standard PCR with the same primers. One of the dNTPs in the PCR mix contains a radioactive label ($^{35}$S or $^{32}$P) for visualisation of the PCR fragments with PAGE. The Liang and Welsh methods rely on at least one small arbitrary primer for selection of specific cDNAs. As a consequence annealing temperatures are low (~40° C.), and all amplified cDNA fragments originate from a certain degree of mismatch priming. Later several groups produced refinements and optimisations leading to a plethora of articles describing the usefulness of the method (Bauer and Warthoe et al. 1993; Warthoe et al. 1995; Liang and Warthoe et al. 1995; Rohde and Warthoe et al. 1996).

OBJECT OF THE INVENTION

It is an object of the present invention to provide new methods and means for investigating the expression patterns in cells, especially in eukaryotic cells. The results of such investigations may be used in drug development, gene discovery, diagnosis of diseases etc., and therefore such improved methods are highly desirable.

SUMMARY OF THE INVENTION

In its broadest scope, the invention pertains to a method for preparing a sub-divided library of amplified cDNA fragments from the coding region of mRNA contained in a sample, the method comprising the steps of a) subjecting the mRNA derived from the sample to reverse transcription using at least one cDNA primer having the general formula $$5\text{-Con}_1\text{-dT}_{n2}\text{-V}_{n3}\text{-N}_{n4}\text{-}3'$$

wherein $Con_1$ is any sequence between 1–100 nucleotides, dT is deoxythymidinyl, V is A, G or C, N is A, G, C or T, n2 is an integer $\geq 1$, n3 is 0 or 1, if n3 is 0 then n4 is 0, and if n3 is 1 n4 is an integer $\geq 0$, thereby obtaining first strand cDNA fragments, b) synthesizing second strand cDNA complementary to the first strand cDNA fragments by use of the first strand DNA fragments as templates, and a second cDNA primer with the general formula $$5'\text{-Con}_2\text{-N}_{x}\text{-}3'$$

wherein $Con_2$ is any sequence between 1–100 nucleotides and can be different or identical to $con_1$, $N_x$ is A, G, T or C, and x is an integer ≧0, in a appropriate enzyme/-buffer solution which comprises the DNA pol I enzyme or the Klenow fragment of the DNA pol I enzyme, all four deoxyribonucleoside triphosphates and standard buffer and temperature conditions, thereby obtaining double stranded cDNA fragments, c) subjecting the cDNA fragments obtained in step b) to a molecular amplification procedure so as to obtain amplified cDNA fragments, wherein is used a set of amplification primers having the general formula

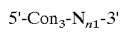
$$5'\text{-Con}_3\text{-N}_{n1}\text{-}3'$$

wherein $Con_3$ is a sequence identical to either $Con_1$ or $Con_2$ or both, N is A, G, T or C, and n1 is an integer ≧0, wherein at least one set of primers has the general formula I where n>0, said at least one set being capable of priming amplification of any nucleotide sequence complementary in its 5'-end to $Con_1$ or $Con_2$.

This method is advantageous for amplifying very small amounts of RNA. Using the method of the invention it is possible to perform gene-profile analysis from less than 100 cells equal to $10^{-9}$ gram total RNA (10 pgram RNA per cell).

In a further aspect, the invention relates to a method for preparing a sub-divided library of amplified cDNA fragments from the coding region of mRNA (which may be of prokaryotic, Archae or eukaryotic origin) contained in a sample, the method comprising the steps of a) subjecting the mRNA derived from the sample to reverse transcription using at least one cDNA primer, thereby obtaining first strand cDNA fragments, b) synthesizing second strand cDNA complementary to the first strand cDNA fragments by use of the first strand DNA fragments as templates, thereby obtaining double stranded cDNA fragments, c) digesting the double stranded cDNA fragments with at least one restriction endonuclease, thereby obtaining cleaved cDNA fragments, d) ligating at least two adapter fragments to the cleaved cDNA fragments obtained in step c), so as to obtain ligated cDNA fragments, and e) subjecting the ligated cDNA fragments obtained in step d) to a molecular amplification procedure so as to obtain amplified cDNA fragments, wherein is used, for an adapter fragment used in step d), a set of amplification primers having the general formula

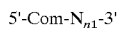
$$5'\text{-Com-N}_{n1}\text{-}3' \qquad \qquad II$$

wherein Com is a sequence complementary to at least the 5-end of an adapter fragment which is ligated to the 3'-end of a cleaved cDNA fragment, N is A, G, T, or C, and n1 is an integer ≧0, and wherein at least one set of primers has the general formula II where n1>0, said at least one set being capable of priming amplification of any nucleotide sequence ligated in its 3'-end to the adapter fragment complementary in its 5'-end to Com.

The overall advantage of the invention compared to the prior art is that the resulting library of cDNA fragments contains nucleic acid sequences from all parts of cDNA which is produced in step a). Prior art techniques which i.a. rely on poly-dT cDNA priming have a tendency to only yield fragments derived from the long untranslated regions of mRNA. Furthermore, by fine-tuning of the conditions in each step, the method of the present invention results in highly specific reproduction of sequence information which is present in mRNA, even in mRNA which is only present in relatively low amounts. Furthermore, by choosing the optimum composition of endonuclease(s) it is possible to obtain cDNA fragments which are derived from a very large percentage of the total number of transcribed genes in relevant cells.

The present method allows the targeted visualisation of known genes by using primer combinations, corresponding to sequences from the gene of interest. This has the advantage that all steps of the procedure and the biological system can easily be verified. Also, very specific expression analyses can be carried out on related genes with very high homology which could not be achieved by using hybridisation technology.

Briefly, further steps in the method of the invention involve isolation of bands of interest from a gel, their cloning and sequencing. The sequence information allows re-amplification of individual bands, using primers with the appropriate 3–4 nucleotide extensions. When run on a gel, these reactions will show one, or only a few, bands per lane, giving an unequivocal determination of band identity.

Since the present technology makes use of end labelled primers for visualization, the technology can be used, both with standard technologies involving radioactivity, or with fluorescent labelled primers, without the need for further optimisation.

The invention also pertains to methods for detecting differences between expression level(s) in cells which have been subjected to different conditions, methods for diagnosing disease, and methods related to "bioinformatics" wherein are used a combination of output from the above-disclosed method and data obtained by computer-simulation of corresponding treatment of well-defined stretches of nucleic acids.

A separate part of the invention pertains to a novel method for performing reverse transcription, methods which yield considerably enhanced quality in the reversely transcribed material. Also means for carrying out this separate part of the invention are disclosed.

In the following is given a short discussion of terms used in the present application:

"A sub-divided library of amplified cDNA fragments" is in the present context a library of amplified cDNA fragments which is split into a number of separate pools, each pool being defined by the sequences of the termini of the amplified fragments. For example, one pool may contain amplified fragments which are all characterized by having the sequence 5'-Com-AGC- in one of the strands, whereas another pool contains amplified fragments having the sequence 5'-Com-AAT in one of the strands. For a discussion of the meaning of "Con" and "Com", cf. below.

"A normalised library" is a library containing substantially equal representation of each mRNA, i.e. approximately the same number of copies of each mRNA.

"Reverse transcription" has its usual meaning in the art, i.e. synthesis of DNA using RNA as a template and effected by an enzyme having reverse transcriptase activity.

"Adapter fragment" is intended to mean a nucleic acid sequence containing a known sequence which can be used as template for a primer in a subsequent molecular amplification procedure such as PCR. The adapter fragment is further characterized by its ability to become integrated at the end of a cDNA fragment which has previously been cleaved with a restriction endonuclease in step c). In most cases, the restriction endonuclease leaves fragments having "sticky ends", to which the adapter fragment will anneal readily, and thereafter the adapter fragment becomes ligated to the cDNA by the action of a DNA ligase.

DETAILED DISCLOSURE OF THE INVENTION

In the following, the impact of each of the steps will be discussed in detail, see FIGS. 1 and 7.

Step a)

The goal in step a) is to produce a mixture of first strand cDNA fragments which is optimized in its composition for carrying out the subsequent steps. A number of considerations apply:

First of all, to reduce the "background noise", it is preferred that the annealing of cDNA primer to the RNA in step a) is performed under high stringency conditions, thereby ensuring that a minimum of mismatches are introduced in the cDNA relative to the mRNA, i.e. at a temperature above 50° C.

Secondly, it is desirable to obtain copies of sequences which are derived from all parts of mRNA in order to obtain information relating to the translated part of the mRNA. Prior art methods for reverse transcription of eukaryotic material have often utilised poly-dT as cDNA primers. This strategy has, however, the disadvantage that the most efficiently reverse transcribed material is situated in the untranslated part of the genes of interest. Hence, the only parts of the mRNA which become "visible" after e.g. a PCR procedure will very often be derived from untranslated regions of the RNA. The reason for this is two effects. First of all, the poly-dT approach has the consequence that the initiation point of reverse transcription is situated very far from e.g. the start codon relating to the operon in question. Secondly, the mRNA may include structures (e.g. "hairpin" structures due to intra-chain base-pairing) which block reverse transcription and by always initiating reverse transcription at one terminus of a gene, such structures will statistically block reverse transcription of a number of translated regions.

It is in the present invention preferred to ensure that cDNAs are produced in step a) which are representatives of the entire gene, including the translated regions. This can be obtained in a number of ways. If poly-dT priming (or a variation thereof) is used, it is preferred to perform the reverse transcription at an elevated temperature, e.g. in the range from about 45° C. to about 95° C., and to use an enzyme having reverse transcriptase activity at said temperature. Normally the temperature will be higher than 45° C., e.g. at least 50° C., or even higher, e.g. at least 55° C., at least 60° C., at least 65° C. or even higher, e.g. at least 70° C. This approach has the effect that the elevated temperature ensures that e.g. hairpin structures are "stretched out" during the reverse transcription step, thereby avoiding the lack of reversely transcribed fragments upstream of such structures.

Known enzymes having reverse transcriptase activity at such elevated temperatures are enzymes selected from the group consisting of DNA polymerases derived from thermophilic eubacteria, such as the polymerases Taq (*Thermus aquaticus*), Stoffel (*Thermus aquaticus*), Tth (*Thermus thermophilus*), Tfl/Tub (*Thermus flavus*), Tru (*Thermus Ruber*), Tca (*Thermus caldophilus*), Tfil (*Thermus filiformis*), Tbr (*Thermus Brockianus*), Bst (*B. Stearothermophilus*), Bca (*B. Caldotenax* YT-G), Bcav (*B. Caldovelox* YT-F), FjSS3-B.1 (Thermotoga FjSS3-B.1), Tma (*Thermus Maritima*), UlTma (*T. Maritima*), Tli (*T. Litoralis*), Tli exo- (*T. Litoralis*), 9° N-7 (Thermococcus sp.), BG-D (Pyrococcus sp.), Pfu (*P. furiosus*), Pwo (*P. woesei*), Sac (*S. Acidocaldarius*), SsoI (*S. Solfataricus*), Tac (*T. Acidophilum*), and Mth (*Methananococcus Voltae*).

One minor disadvantage of using these thermostable enzymes is that they have a tendency to be relatively ineffective compared to the "traditional" non-thermostable, reverse transcriptases. Hence, especially if priming of the reverse transcription is not limited to the use of poly-dT primers, it is according to the invention possible to use non-thermostable, reverse transcriptases. Hence, in other preferred embodiments, the reverse transcription is carried out at a temperature in the range from about 25° C. to about 55° C. by use of an enzyme having reverse transcriptase activity at said temperature. Normally the temperature will not exceed 50° C., and usually it will be lower, such as at most 47° C., at most 45° C., at most 43° C., at most 40° C., and at most 35° C. The reverse transcriptase can e.g. be selected from the group consisting of the reverse transcriptases from AMV (Avian Myeloblastosis Virus), M-MuLV (murine M-MULV pol gene), and HIV-1 (HIV virus).

According to the invention, the most preferred way of carrying out step a) is to carry out reverse transcription in two subsequent steps, the first step comprising carrying out reverse transcription at the temperature conditions described above for non-thermostable enzymes, and the second step comprising carrying out reverse transcription at the temperature conditions described above for thermostable enzymes. Normally this can be accomplished by having two non-identical enzymes present in the reverse transcription reaction, especially because the non-thermostable enzyme will be inactivated by the increase in temperature which is introduced when going into step 2. Of course, the enzymes can be added for each reaction step, but it is preferred that both enzymes are present from the start of the reaction.

It is especially preferred that the activity of the enzyme which is active in the first step is substantially abolished in the second step (e.g. as a consequence of temperature denaturing of that enzyme), or expressed otherwise, that in the second step the enzyme used in the first step is substantially inactive. In general, it is preferred that the enzymes used in each step are substantially more active in the relevant temperature range than the one wherein the other enzyme is used.

In a preferred embodiment the reaction mixture with the sample comprises a cDNA primer, said cDNA primer being sufficiently complementary to the target RNA present in the sample to hybridize therewith and initiate synthesis of a single stranded cDNA molecule complementary to said target RNA and the reaction mixture comprises an appropriate buffer which comprises all four deoxyribonucleoside triphosphates and a divalent cation selected from the group of $Mg^{+2}$ and $Mn^{2+}$ in a concentration between 0.01.1 and 5 mM.

In fact, it is believed that the above strategy for conducting reverse transcription by use of two enzymes having different temperature optima and of which one has a temperature optimum at which impeding structures in the RNA are "stretched out", is novel and inventive in its own right.

Preferred combinations of enzymes in this embodiment of the invention are that the enzyme effecting reverse transcription in the first step is MMuLV, AMV, HIV-1 and/or the enzyme effecting reverse transcription in the second step is Tth or Taq.

An object of the method of the invention is to obtain a subdivision of the cDNA produced. When the mRNA is derived from a eukaryotic system, the at least one cDNA primer may include an oligo or poly dT tail in the 5'-end, having the general formula 5'-$dT_{n2}$-$V_{n3}$-$N_{n4}$-3', wherein dT is deoxythymidinyl, V is A, G, or C, N is A, G, C, or T, n2 is an integer $\geq 1$, n3 is 0 or 1, if n3 is 0 then n4 is 0, and if n3 is 1 then n4 is an integer $\geq 0$. It will be clear that when n3 and n4 are both zero, then the primer is an ordinary poly- or oligo-dT cDNA primer. However, when n3 is 1, then the primer is in fact a primer composition which will be able to prime the reverse transcription of any mRNA having a poly-A tail. If the original sample of RNA is subdivided, and each sub-pool is subjected to reverse transcription which uses one of the possible primers having the above formula where n3 is 1, then the result is a number of single stranded cDNA pools which are each different from each other in the 5'-end.

For example, when n3 is 1, $3\times4^{n4}$ groups of cDNA primers are used, each group being distinct from any one of the other groups with respect to the structure $-V_{n3}-N_{n4}-$. In such an embodiment the pool of mRNA is conveniently subdivided into $3\times4^{n4}$ aliquots which are each subjected separately to step a) utilising one of the $3\times4^{n4}$ groups of cDNA primers, thereby obtaining a subdivision of the first strand cDNA into $3\times4^{n4}$ separate pools. Normally n4 will be 0 or 1, resulting in the provision of 3 or 12 pools, respectively.

When the starting material is not eukaryotic or when it is not the intention to necessarily set out from the part of the transcribed gene which is most remote relative to the translation start codon, the at least one cDNA primer does not include a poly or oligo dT tail in the 5'-end, or, alternatively, at least two cDNA primers are used of which at least one includes a poly or oligo dT tail in the 5'-end and of which at least one second does not include a poly or oligo dT tail in the 5'-end. Preferably, the cDNA primer which does not include a poly or oligo dT tail in the 5' end has the following structure $5'-N_xTTA-3'$ or $5'-N_xCTA-3'$ or $5'-N_xTCA-3'$, wherein N is A, G, T, or C, and x is an integer $1 \leq x \leq 20$. It will be clear that this corresponds to cDNA priming setting out from any translation stop codon. As for the above embodiments utilising a poly- or oligo-dT tailed primer, it is, by preparing primers having all possible permutations represented in the group $N_x$, possible to compose the primers so as to correspond to any possible sequence preceding a stop codon, thereby ensuring priming of all sequences having a stop codon in their sequence.

Step b)

This step is carried out by methods well known in the art. It is, however, preferred that step b) is carried out under conditions which minimize the formation of mismatches between nucleotides in the first and second cDNA strands. The double stranded cDNA procedure can be performed according to standard methods as described in Sambrook et al. (1989). However since standard polymerases can have difficulty in synthesising regions containing secondary structures or with high GC-content, thermostable RNase H (Hybridase Thermostable RNase H, U.S. Pat. No. 5,268,289) and thermostable rBst DNA polymerase from Bacillus stearothermophilus help overcome some of the limitations that standard polymerases (low temperature polymerases) suffer from.

Step c)

In one embodiment of the invention the ligated cDNA fragments obtained in step b) are subjected to a molecular amplification procedure so as to obtain amplified cDNA fragments, wherein is used a set of amplification primers having the general formula $5'-Con_3-N_{n1}-3'$ wherein $Con_3$ is a sequence identical to either $Con_1$ or $Con_2$ or both, N is A, G, T or C, and n1 is an integer a 0, wherein at least one set of primers has the general formula I where n>0, said at least one set being capable of priming amplification of any nucleotide sequence complementary in its 5'-end to $Con_1$ or $Con_2$.

In another embodiment, after the preparation and optional subdivision of the mRNA, each of the different pools of cDNA is digested with at least one restriction enzyme to produce fragments of a size which can be separated using an appropriate size fractionation method.

The choice of restriction enzyme is based largely on the frequency of the cleavage sites in a given cDNA pool. Too many cleavage sites in each cDNA fragment will result in too small fragments, and vice versa. Optimally, the at least one enzyme should cleave every cDNA to yield fragments of the desired size. Statistically, it is not possible to cleave every cDNA, but on the other hand a very large percentage can be cleaved by choosing a suitable enzyme or combination of enzymes. It is preferred that the method of the invention utilises at least one restriction enzyme chosen so as to ensure that at least 60% of cDNA's are cleaved, but higher percentages such as at least 65%, at least 70%, at least 75%, at least 80%, or even at least 85% are more preferred.

Preferably the invention should use restriction enzymes that leave protruding ends (sticky ends) at the termini of the DNA after digestion in step c), since this greatly facilitates the introduction of the adapter fragments in step d).

As will appear from the above, the frequency with which the restriction endonuclease cleaves is important. The at least one restriction enzyme is preferably chosen so as to cleave each complete cDNA into an average of about 3 fragments. It will be understood that some cDNAs obtained from preceding steps will not be cut at all (although this is a rare incidence when the restriction enzyme(s) is/are carefully chosen) whereas others will be cut with a high frequency. It has come out that use of a rare 4 base cutter as at the least one restriction endonuclease (such as the 4 base cutter AciI, AluI, BfaI, BstUI, Csp6I, DpnI, DpnII, HaeIII, HhaI, HinPII, HpaII, MboI, MnlI, MseI, MspI, NlaIII, RsaI, Sau3AI, TaiI, TaqI, and Tsp509I) ensures the optimum performance of the inventive method. By use of such a rare 4 base cutter, the use of only 1 restriction enzyme in step c) is sufficient and results in superior output.

Alternatively, a combination of restriction endonucleases can be used wherein a balance of e.g. 6 base cutters and 4 base cutters ensures a reasonable distribution of fragment sizes. For instance the use of a first restriction enzyme (e.g. a 6 base cutter) which statistically cleaves at least 20% of complete cDNA derived from the mRNA sample into two subfragments, and of a second restriction enzyme (e.g. a 4 base cutter) which statistically cleaves at least 50% of said subfragments into 3 further subfragments, will also result in a series of fragments suitable for later size fractionation.

Step d)

The mixture(s) obtained in step c) are then subjected to a reaction wherein adapter fragments are added to both ends of the double stranded cDNA fragments obtained. As mentioned above, this part of the procedure is greatly facilitated by the cleaved cDNA fragments having protruding "sticky" ends, because pre-designed adapter fragments which fit to these protruding ends can easily be prepared.

The adapter (or anchor) fragments are added to the cleaved fragments in order to obtain "order in chaos" in the subsequent step. By adding known sequences to the termini of the cleaved fragments, one creates targets for specific amplification primers which can be designed specifically with the aim of amplifying sequences complying to the adapter fragments. The material thus obtained (primary template) can be pre-amplified, using primers complementary to the ligated adaptor sequences, giving rise to secondary template. The pre-amplification of primary template allows virtually unlimited amounts of template to be produced from one RNA preparation, avoiding the need for repeated isolations.

The adaptor sequence is thus selected so as to serve as the starting point for DNA polymerisation in e.g. a PCR reaction. The adaptor sequences are constructed in such a way that the specific endonuclease sites are not regenerated after ligation of said adaptor.

In a preferred embodiment at least one termination fragment is also ligated to the 3'-end of single strands of cleaved cDNA fragments, said at least one termination fragment introducing a block against DNA polymerization in the 5'→3' direction setting out from the at least one termination fragment and said at least one termination fragment being unable to anneal to any primer of the at least two primer sets in step e) during the molecular amplification procedure.

The above is a very important procedure when combined with the use of detection effected by labelled primers in the amplification step, wherein only one member of the pair of primers is labelled whereas the other is designed to split up the amplified products according to their base composition adjacent to the adapter fragment. One important feature is that a single stranded cDNA fragment which has been provided with a termination fragment will not be amplified, because no primers will be able to anneal to the products of a first round polymerisation wherein such a fragment was the template, see FIG. 7. Secondly, the approach opens for the possibility of removing background "noise" in a subsequent detection phase.

Normally, the at least one termination fragment comprises or is a chemically modified nucleotide sequence, such as for instance a nucleotide sequence which comprises a dideoxynucleotide in the 3'-end; this termination technique is well-known from e.g. the chain-termination sequencing technique according to Sanger. Under normal circumstances, the dideoxynucleotide should, according to the invention, be covalently attached to the nucleotide strand so as to avoid loss of the dideoxynucleotide during subsequent rounds of amplification. Superior stabilisation is attained if the dideoxynucleotide is phosphorylated.

As mentioned above, the ligation of adapter and/or termination fragments to the cleaved cDNA fragments in step d) is conveniently achieved by annealing the adapter fragments to sticky ends of the cDNA resulting from the cleavage in step c) and subjecting the product to the action of an enzyme having DNA ligase activity. Any suitable DNA ligase known in the art can be used.

Step e)

Step e) of the method of the invention results in the final sorting of the modified cDNA fragments from step d). As steps b), c) and d) are combined in the broadest embodiment of the invention, step e) corresponds to step c) of this embodiment described above.

The primers having the structure of formula I (step c) or II (step e) are designed so as to selectively amplify synthesized double stranded cDNA fragments obtained in step b) or predefined subsets of the adapted fragments obtained in step d). A number of ways this can be done may be envisaged, but the main strategy is to prime amplification in a series of separate reactions where the nucleotide sequence of one primer in one reaction ensures that the amplified products of that reaction are different from those obtained from any of the other reactions and that all the reactions result in amplification of all fragments obtained from step b) or d), respectively.

Even though the at least one set of amplification primers of formula I or II wherein has a n1 which is $\geq 0$, it is preferred that n1=1, n1=2, n1=3, or n1=4 in one of the primers, because the number of primer fragments to be used in the reactions in order to cover all possible nucleotide stretches adjacent to the Con or adapter fragment is easily manageable. For instance, if n1=5, it would be necessary to use $4^5$=1024 different primers in order to obtain amplification of all possible nucleotide sequences adjacent to the relevant adapter fragment, and since the preferred embodiment of the invention requires that each such primer is used in a separate reaction, the work involved would be problematic.

It is also preferred that in one of the primers n=0, and it is especially preferred that this primer is labelled, in order to facilitate determination of the amplified fragments.

Hence, in the most preferred embodiments of the invention, the adapted cDNA fragments are amplified in a number of separate reactions wherein a labelled primer is used (which is normally identical in all reactions) and at least one nonlabelled primer which is a member of the set of primers described above where n>1. It is preferred that this set of amplification primers of formula I or II wherein n1>0 comprises all possible combinations and permutations of A, G, T, and C in the group $N_{n1}$, since this will ensure that all possible cDNA fragments can be amplified by the set.

Hence, the ligated cDNA fragments are sub-divided into a number of pools prior to the molecular amplification in step e), and each pool is subjected to the amplification using a subset of the set of amplification primers, and in the most preferred embodiment the ligated cDNA fragments of step d) are subdivided into $4^{n1}$ pools which are each subjected separately to step e) wherein is used one amplification labelled primer as described above (n1=0) and one primer from the set of amplification primers as defined above (n>0), said one primer being distinct from any one of the primers used for amplifying any of the other pools. By using this approach, the originally reverse transcribed and cleaved cDNA fragments are subdivided into $4^{n1}$ pools which can each be subjected to further steps.

Further Steps and Applications

The material obtained from the above-described series of reactions can now be utilised in a number of ways. Normally, a further step of separating amplified fragments obtained from the molecular amplification procedure is performed. This yields a mixture of amplified fragments which are separated e.g. by size separation, by mobility in a gel electrophoresis or by any suitable chromatographic method. Furthermore, a step of identification (e.g. by visualization of these separated fragments) is normally carried out for "book-keeping purposes"; the separated mixture of fragments will normally be compared to some kind of reference which may be material derived from the same or another cell type.

Visualization of the separated fragments can, as mentioned above, be achieved by one of the primers in the amplification reaction being labelled, but other methods are of course available. For instance, a specifically labelled probe which e.g. binds to one of the adapter sequences will visualise the fragments, but also labelled nucleotides which have been incorporated in the fragments during the amplification procedure (e.g. a PCR) will of course be a suitable means for detection (e.g. by incorporating radioactive or fluorescent alpha dNTP into the cDNA fragment during PCR, where N=A, C, T, U or G).

However, it is preferred that visualisation of specific RNA Derived Fragments (RDFs) is achieved using primers which are radioactively or fluorescently labelled and are homologous to the adaptors. The comparatively high annealing temperatures (touch-down from 65° C. to 56° C.) which are preferably used ensure that polymerisation events will predominantly originate from perfect priming of adapter sequences and adjacent selective bases. Band intensities are largely a function of initial template concentration, whereas band intensities of the original Differential Display methods are dependent on the quality of the match between the individual template and primer. The visualisation of rare mRNAs using the present inventive methods will be less hampered by the over-representation of signal from highly abundant mRNAs. As in the case of arbitrary priming, the mismatch amplification and abundant RDFs always outcompete the amplification of rare fragments base pair perfectly. Our experiments suggest that as few as 100 molecules can be routinely detected in a given template. This corresponds to less than 1 transcript per cell in the original tissue.

One interesting part of the invention relates to the use of the above-described methods in bio-informatics. In short, known DNA sequences are inputted into a computer database, and on the basis of such sequences a comparison with a real-life run of the above-described methods can be performed. In this way, bands in a gel obtained from the methods of the invention can be unambiguously identified with respect to sequence, origin and even functionality. Hence, this part of the invention pertains to a method for determining the presence of an expression product in a cell or group of cells, the method comprising providing an RNA-containing sample from the cell or group of cells and subjecting the sample to the method described above, and thereafter performing a comparison of the thus identified amplified cDNA fragments with a database output, said database output comprising a computer-generated list of molecular weights of restriction DNA fragments of known sequences, said list being prepared by inputting and storing DNA sequence data in a database as virtual DNA sequences (these can be obtained and updated regularly from any database containing information about gene sequences from the relevant organism or cell type), subsequently simulating cleavage of the virtual DNA sequences with the at least one restriction nuclease and storing the resulting simulated cleavage products as virtual cleaved DNA fragments (such simulation is relatively uncomplicated, since the recognition and cleavage patterns of a large number of restriction enzymes are already known), simulating ligation to the virtually cleaved fragments of the at least two adapter fragments and storing the results as virtually ligated DNA fragments (again, this merely requires that input is provided of the structure of adapter fragments used in the real-life process), for each individual combination of primers used in step e) grouping the virtually ligated DNA fragments susceptible to amplification by said combination of primers in the same group, determining, in each group, the absolute and/or relative molecular weight of each virtually ligated DNA fragment, and outputting the content of each group in the form of a list comprising the absolute and/or relative molecular weights of the virtually ligated fragments in the group.

It is preferred that a link is maintained between each member of the output list and the original sequence from which such a member has been derived. This can e.g. be done by linking the input DNA sequence data to data relating to the genetic origin of the DNA sequence data and optionally to data relating to functional features relating to the genetic origin and thereafter maintaining the information as a pointer back in the system to said sequence. Hence, the output indication will conveniently further comprise information about the genetic origin of the virtually ligated DNA fragment and optionally information about functional features associated with the genetic origin.

For ease of use of such a bio-informatic system, it is normally necessary that 1) either the comparison is performed by inputting the identified amplified cDNA fragments in a format which allows automated comparison with the database output, or 2) the database output is outputted in a format which allows for direct comparison between the separated amplified cDNA fragments and the database output. For instance, if the visualized and separated cDNA fragments from step e) have been run on a gel, it will be possible to either read a digital reproduction of the gel pattern into the computer and let the computer compare this input with the computer generated pattern, or alternatively, to output the computer generated pattern in such a manner that it resembles an electrophoresis gel pattern.

Another part of the invention pertains to the use of the inventive method for comparing expression levels in different cells. One way of doing this is to determine the change in expression, compared to the expression in a reference cell or reference group of cells, of an expression product in a cell or group of cells which has been subjected to a first set of conditions influencing the expression pattern of said cell or group of cells, said reference cell or group of cells being subjected to a second set of conditions, the method comprising providing an RNA-containing sample from the cell or group of cells and subjecting the sample to the method of the invention for sub-division, thereby obtaining data describing the amplified cDNA fragments derived from the sample, providing reference data describing amplified cDNA fragments derived from an RNA-containing reference sample from the reference cell or reference group of cells, the reference data being obtained by having previously subjected the reference sample to the method of the invention, subsequently performing a comparison of the data and the reference data to identify the cDNA fragments which are expressed at different levels in the two data sets, and thereafter using the differentially expressed cDNA fragments to determine which expression products are subject to a change in expression level. In other words, the method of the invention is carried out twice on the basis of two different RNA samples derived from cells subjected to differing conditions.

Normally, the data and reference data are selected from the group consisting of the apparent molecular weights of the amplified DNA fragments, the $M_r$ of the amplified DNA fragments, the absolute amount of the amplified DNA fragments, and the relative amounts of the amplified DNA fragments. The reference data can further be extracted from a database containing the reference data defined above and optionally further information relating to the genetic origin of each amplified cDNA fragment from the reference.

Related to the above, the invention also allows for diagnosis of disease which is characterized by a deviating (increased or reduced) expression level of at least one expression product in at least one cell type, the method comprising providing an RNA-containing sample derived from the at least one cell type, subjecting the sample to the method of the invention thereby obtaining data describing the amplified cDNA fragments derived from the sample, providing reference data describing amplified cDNA fragments derived from a RNA-containing reference sample derived from the same type of cell from a subject not suffering from the disease, the reference data being obtained by having previously subjected the reference sample to the method according to the invention, and subsequently performing a comparison of the data and the reference data with respect to those cDNA fragments which are known to be related to the disease, and assessing whether a significant difference in the data and reference data exists so as to establish whether the expression level of the expression product deviates or not.

As for the embodiment above, also here the data and reference data are selected from the group consisting of the apparent molecular weights of the amplified DNA fragments, the $M_r$ of the amplified DNA fragments, the absolute amount of the amplified DNA fragments, and the relative amounts of the amplified DNA fragments, and also here the reference data can be extracted from a database containing the reference data defined above and optionally further information relating to the genetic origin of each amplified cDNA fragment from the reference.

Further, the invention provides a method for treatment of a disease which is characterized by a deviating (increased or reduced) expression level of at least one expression product in at least one cell type, the method comprising providing an RNA-containing sample derived from the at least one cell type, subjecting the sample to the method of the invention thereby obtaining data describing the amplified cDNA fragments derived from the sample, providing reference data describing amplified cDNA fragments derived from a RNA-containing reference sample derived from the same type of cell from a subject not suffering from the disease, the reference data being obtained by having previously subjected the reference sample to the method according to the invention, and subsequently performing a comparison of the data and the reference data with respect to those cDNA fragments which are known to be or suspected of being related to the disease, and assessing whether a significant difference in the data and reference data exists so as to establish whether the expression level of the expression product deviates or not.

If the expression product is reduced, the disease may be treated by delivering the expression product; if the expression product is increased, the disease may be treated by delivering an inhibitor (e.g. an antibody) against the expression product. The scope of the present invention includes an expression product identified by the method of the invention as such as well as methods for treating a disease which method has been provided by means of the method of the invention.

The mixtures of amplified fragments obtained from step e) of the method of the invention may also be used for preparing a surface (chip) coated with cDNA fragments. This can be done by subjecting an RNA-containing sample to the subdivision method of the invention including separation steps, and
transferring the separated amplified cDNA fragments to a chip surface adapted to stably bind the separated amplified cDNA fragments while maintaining the spatial relative distribution pattern thereof.

Alternatively, such a chip can be prepared by
subjecting an RNA-containing sample to the method of the invention without performing the separation, and thereafter
separating, by electrophoresis, the thus obtained amplified cDNA fragments on a particular surface adapted to stably bind the separated amplified cDNA fragments while maintaining the relative distribution pattern after electrophoresis. In this embodiment, the electrophoresis is preferably in the form of microelectrophoresis.

Transfer to the surface is preferably accomplished by a electrophoretic blotting technique, and/or by well-known photo-activated organic or inorganic chemistry coupling techniques.

The invention also pertains to a surface obtainable by the above-mentioned method for the preparation thereof. Such surfaces are considered novel and inventive, since known "DNA chips" rely on specific introduction of an array of nucleic acid fragments of known structure, whereas the present method provides for "a semi-array" containing cDNA fragments characterizing a specific "situation" for a specific cell type, according to FIG. 8.

Such a surface can i.a. be used for screening for genes within a gene family. The "array chip" is provided and thereafter a labelled probe (which is a representative of a gene family) is allowed to hybridize to the chip under low stringency i.e. under conditions as described at pages 94–106 in "Nucleic acid hybridisation. A practical approach" edited by B D Hames & S J Higgins, IRL Press. A number of fragments coupled to the chip will hybridize to the probe, and these fragments can subsequently be identified, isolated and sequenced/characterized in order to determine whether they are representatives of the same gene family.

Another use of such "semi-arrays" is for determining the difference in expression pattern between a first cell or type of cells and a second cell or type of cells, the method comprising providing samples of labelled RNA or cDNA from the first and second cells or cell types and subsequently contacting each of these samples with a chip surface as described above, and subsequently detecting the amount and distribution of bound labelled RNA or cDNA from each sample.

Under all circumstances, the chip surface with the cDNA bound thereto can e.g. be produced by the methods described in EP-0 654 061.

Yet another part of the invention pertains to a method for screening for interactions between a pre-selected protein and a polypeptide fragment, the method comprising preparing a sub-divided library of amplified cDNA fragments resulting from step e), optionally adapting the terminals of the members of the library so as to facilitate insertion in a vector, inserting the fragments into vectors, transforming a population of suitable host cells with the vectors, culturing the host cells under conditions which enable expression of correctly inserted cDNA fragments by the host cell, and subsequently assaying polypeptide fragments encoded by the inserted cDNA fragments for interaction with the pre-selected protein.

One convenient way of achieving this is by way of a two-hybrid technique, wherein the host cells are eukaryotic cells (such as fungal cells, especially yeast cells) which are mated or transfected with nucleic acid material encoding the pre-selected protein, successful mating/transfection of the cell(s) resulting in a cell or cells wherein the interaction between the pre-selected protein and a polypeptide fragment gives rise to a detectable signal.

Such methods have recently attracted a great deal of attention, i.a. as a consequence of the disclosure in Fromont-Racine et. al., Nature Genetics 16, 277–282 (1997), which is incorporated by reference herein.

One convenient system for providing the detectable signal is by use of Green Fluorescent Protein, disclosed in EP-A-0 569 170, wherein changes in fluorescent spectrum due to interactions are used as reporter.

Finally, the invention pertains to a composition for use in reverse transcription of RNA, the composition comprising a) a first enzyme having reverse transcriptase activity at temperatures not exceeding 55° C.

b) a second enzyme having reverse transcriptase activity at elevated temperatures in the range of 45° C.–95° C. (and especially the temperatures discussed above for performing reverse transcription at elevated temperatures), said second enzyme having a substantially higher activity than said first enzyme in catalyzing reverse transcription at said elevated temperatures. It is preferred that the first enzyme has a substantially higher activity than said second enzyme in catalyzing reverse transcription at said temperatures not exceeding 55° C., and it is also preferred that the second enzyme has a substantially higher activity than said first enzyme in catalyzing reverse transcription at said temperatures exceeding 45° C.

DESCRIPTION OF THE PREFERRED EMBODIMENTS

BRIEF DESCRIPTION OF THE DRAWINGS

First, the drawing will be briefly described.

FIG. 1

Basis of Display Of Differentially Expressed Transcripts.

FIG. 2

Anchor and PCR primer design.

FIG. 3

An autoradiogram of a DODET gel using the cellular set-up described in Example 1; rat pheochromocytoma PC12 cells were stimulated with the Nerve Growth Factor (NGF) and Epidermal growth factor (EGF).

Lanes 1–24, reverse transcription using the anchored poly T primer 5'-$T_{25}$AA-3'

Lanes 25–48, reverse transcription using the anchored poly T primer 5'-$T_{25}$GC-3'

Lanes 1, 5, 9, 13, 17, 21, 25, 29, 33, 37, 41, 45 represent the PC12 cells not treated.

Lanes 2, 6, 10, 14, 18, 22, 26, 30, 34, 38, 42 and 46 represent the PC12 cells treated with the NGF factor for 60 minutes.

Lanes 3, 7, 11, 15, 19, 23, 27, 31, 35, 39, 43 and 47 represent the PC12 cells treated with the NGF factor for 90 minutes Lanes 4, 8, 12, 16, 20, 24, 28, 32, 36, 40, 44 and 48 represent the PC12 cells treated with the EGF factor for 90 minutes.

Lanes 1–48, using the following pairs for the pre-PCR amplifications SEQ ID NOS: 1 and 2:

TaqI pre-amplification primer: 5'-CAGCATGAGTCCTGACCGA

BclI pre-amplification primer: 5'-CTCGTAGACTGCGTACCGATCA

For the second PCR amplification the following primer pairs were used:

Lanes 1–4 SEQ ID NOS: 3 and 4
5'-CATGAGTCCTGACCGAA
5'-GACTGCGTACCGATCAA (5' end labelling)
Lanes 5–8 SEQ ID NOS: 5 and 6
5'-CATGAGTCCTGACCGAA
5'-GACTGCGTACCGATCAC (5' end labelling)
Lanes 9–12 SEQ ID NOS: 7 and 8
5'-CATGAGTCCTGACCGAA
5'-GACTGCGTACCGATCAG (5' end labelling)
Lanes 13–16 SEQ ID NOS: 9 and 10
5'-CATGAGTCCTGACCGAA
5'-GACTGCGTACCGATCAT (5' end labelling)
Lanes 17–20 SEQ ID NOS: 11 and 12
5'-CATGAGTCCTGACCGAC
5'-GACTGCGTACCGATCAA (5' end labelling)
Lanes 21–24 SEQ ID NOS: 13 and 14
5'-CATGAGTCCTGACCGAC
5'-GACTGCGTACCGATCAC (5' end labelling)
Lanes 25–48
Repeated primer combination from lanes 1–24

FIG. 4a

Northern Blot of RDF01 sequence from cellular total RNA. a) PC12 cells not treated, b) NGF treatment for 60 minutes, c) NGF treatment for 90 minutes, and d) EGF treatment for 90 minutes.

FIG. 4b

Figure 4A:
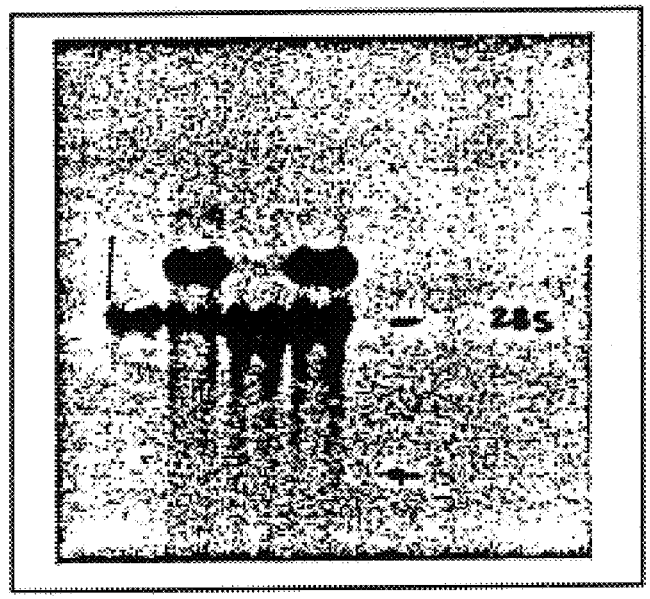
Figure 4B:
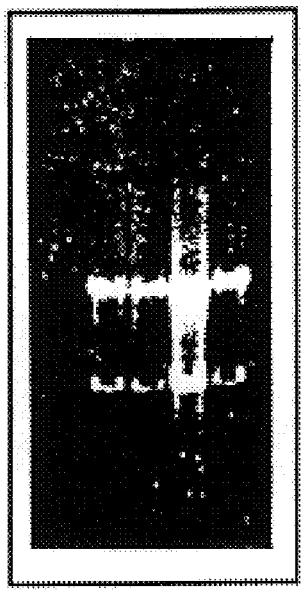

Loading control, RNA extracts were electrophoresed on a 1.2% agarose gel containing ethidium bromide, used as a control to determine the relative concentration of RNA in each lane, a, b, c, d same as in FIG. 4a

FIG. 4c

Northern Blot of RDF02 sequence from cellular total RNA. a) PC12 cells not treated, b) NGF treatment for 60 minutes, c) NGF treatment for 90 minutes, and d) EGF treatment for 90 minutes.

FIG. 4d

Figure 4C:
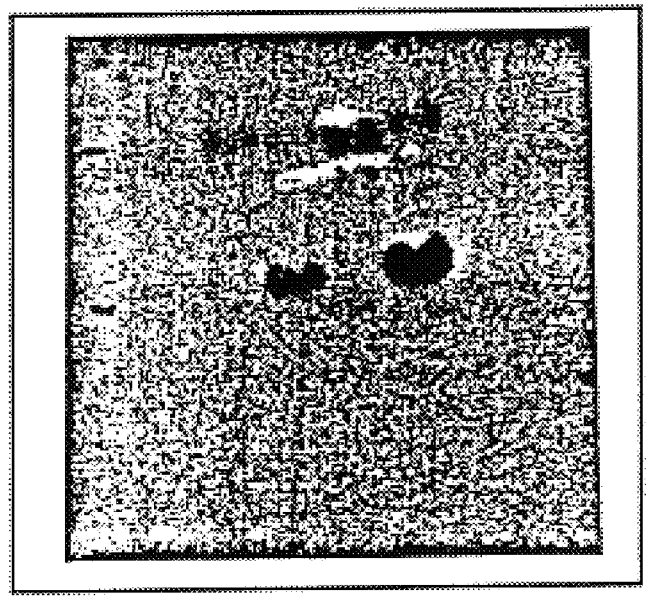
Figure 4D:
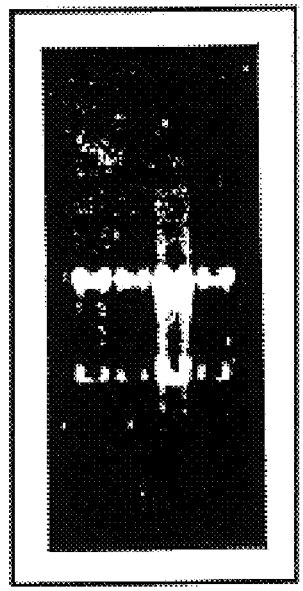

Loading control, RNA extracts were electrophoresed on a 1.2% agarose gel containing ethidium bromide, used as a control to determine the relative amount of RNA in each lane, a, b, c, d same as in FIG. 4c

FIG. 5

Searching for genes modulated by a growth factor.

Lane 1 Size marker in bp (150 bp, 200 bp, 250 bp).

Lanes 2–6 Amplification primer 5'-Com-$N_{n1}$-3' where $N_{n1}$ is GAA

Lanes 7–11 Amplification primer 5'-Com-$N_{n1}$-3' where $N_{n1}$ is GAC

Lanes 12–16 Amplification primer 5'-Com-$N_{n1}$-3' where $N_{n1}$ is GAG

Lanes 17–21 Amplification primer 5'-Com-$N_{n1}$-3' where $N_{n1}$ is GAT

Lanes 22–26 Amplification primer 5'-Com-$N_{n1}$-3' where $N_{n1}$ is GCA

In lane 11 a downregulation is observed after 6 days treatment, whereas in lane 16 an upregulation is observed after 6 days treatment. Both modulations are due to the growth factor, since regulation is seen only when the active growth factor is present.

FIG. 6

Searching for genes involved in bacterial resistance.

Lane 1: Size marker in bp (150 bp, 200 bp, 250 bp, 300 bp).

Lanes 2–5 Amplification primer 5'-Com-$N_{n1}$-3' where $N_{n1}$ is GAA

Lanes 6–9 Amplification primer 5'-Com-$N_{n1}$-3' where $N_{n1}$ is GAC

Lanes 10–13 Amplification primer 5'-Com-$N_{n1}$-3' where $N_{n1}$ is GAG

Lanes 14–17 Amplification primer 5'-Com-$N_{n1}$-3' where $N_{n1}$ is GAT

Lanes 18–21 Amplification primer 5'-Com-$N_{n1}$-3 where $N_{n1}$ is GCA

Lanes 22–25 Amplification primer 5'-Com-$N_{n1}$-3' where $N_{n1}$ is GCC

In lanes 8–9 a downregulation is observed, in lanes 20–21 an upregulation is observed. Both gene modulations are potential genes involved in the resistance to the Bacteriamycin, Inosin.

FIG. 7

Principle of the technology used in Examples 4 and 5.

After ds-cDNA synthesis the DNA is digested with one 4 base pair endonuclease and anchors are ligated to the ds-cDNA ends. Using special design primers the expression profiles are obtained by amplifying the mRNAs in different expression windows (sub-fractions). The number of expression windows depends on the complexity of the sample i.e. 64 expression windows in eukaryotic.

FIG. 8

Principles of a gene discovery DNA surface (a DNA chip).

Figure 7:
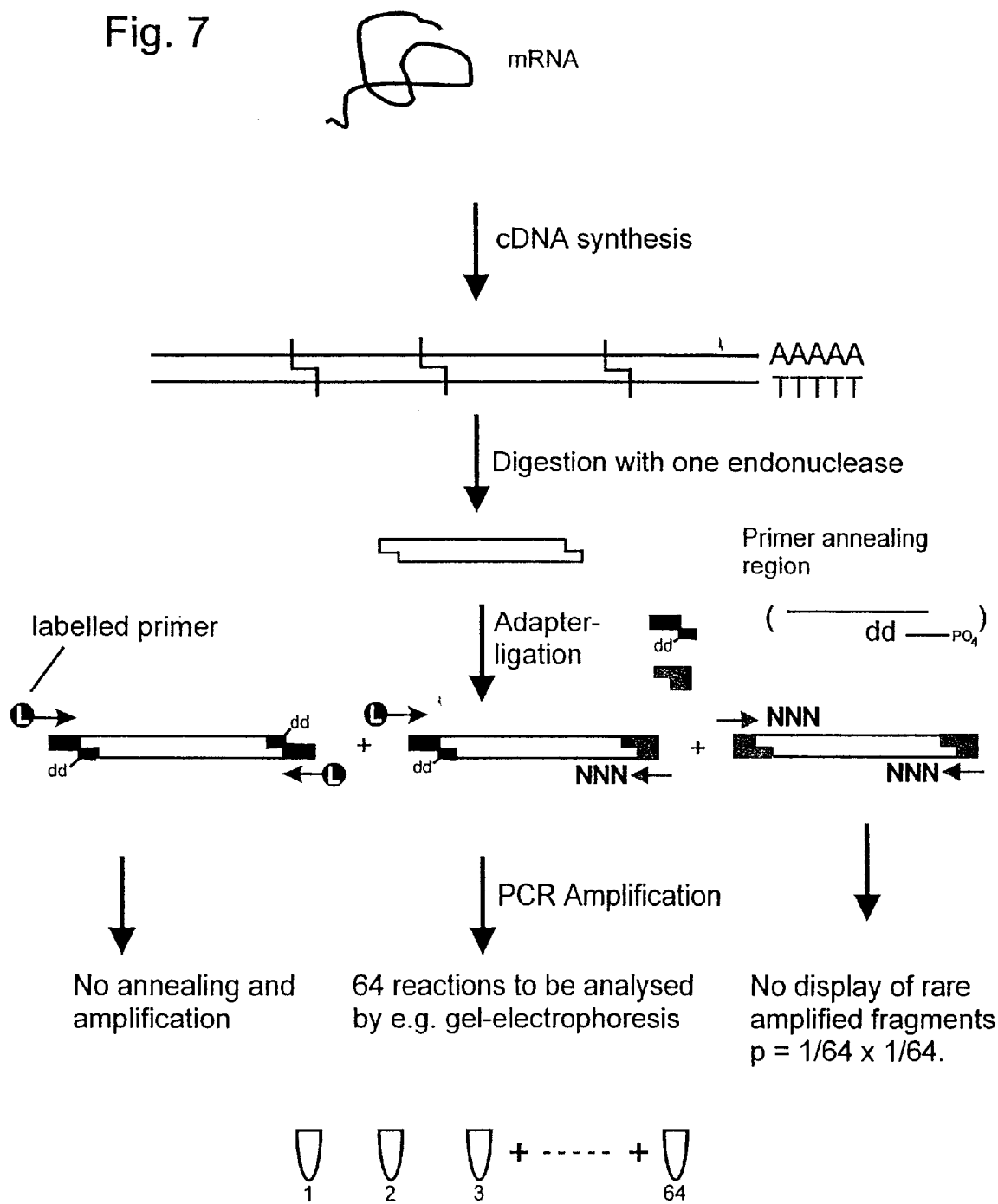
Figure 8:
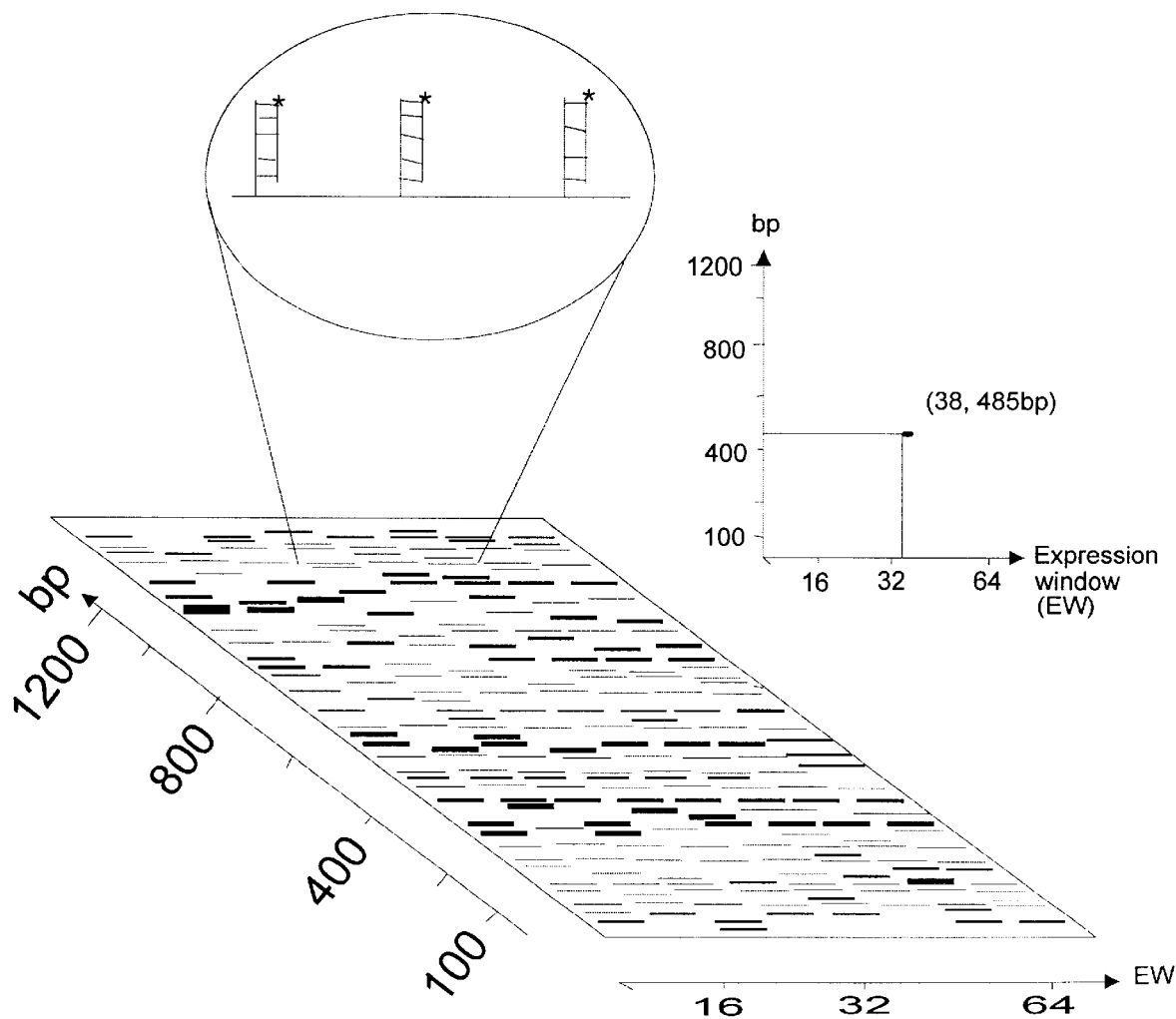

After size separation of the DNA fragments, the DNA fragments are transferred to a nylon membrane using an electrophoretic principle. The membrane is hybridized with a complex DNA probe generated using the principle of the invention. Alternatively the membrane can be hybridized with one single gene to identify new members of a particular gene family. The membrane are in the x coordinates separated in 64 expression windows, and in the y coordinates separated in base pair size (from 50 base pair to 1200 base pair) according to principle described in FIG. 7.

FIG. 9

Principle of generation 64 pools of 3' END cDNAs

Step 1

Production of single stranded cDNA using 5'-$con_1$-$T_n$V oligonucleotide where $con_1$ is an oligonucleotide between 1–100 nucleotide, n is between 5–40 and V is a mixture of A, C and G.

Step 2

Double stranded cDNA synthesis are produced using 5' $Con_2N_x$ where $con_2$ is an oligonucleotide between 1–100 nucleotide, x is between 1–10, and N is a mixture of A, C, T and G. The ds-cDNA synthesis is synthesized by Klenow enzyme with the above-described oligonucleotide.

Step 3

Pre-amplification of double stranded cDNA to amplify the double stranded cDNA, the cDNA is PCR amplified using a combination of $con_1$ and $con_2$ primers.

Step 4

The pre-amplified cDNA is further amplified and separated in 64 pools using a combination of a labeled $con_1$ and 64 $con_2$NNN primers in a PCR amplification procedure, where NNN are combined in 64 different ways using the nucleotides A, T, G and C.

Step 5

Each of the 64 pools is separated using the Page electrophoresis principle.

EXAMPLES

In order to verify the functionality of the invention, examples are described below in which a developmental eukaryotic cellular system, pheochromocytoma PC12, was employed.

Nerve Growth Factor (NGF) induces growth arrest and neurone outgrowth in the in vitro PC12 cell system. Other growth factors, such as epidermal growth factor (EGF), support survival and stimulate growth. NGF-induced genes, include the immediate early genes, which encode transcription factors, such as c-fos and c-myc. The products of the immediate early genes are thought to be involved in regulating the expression of genes, associated with the neuronal phenotype for example neurofilaments, peripherin, GAP43 and transin.

In order to identify new early genes involved in neuronal differentiation and proliferation, the following DODET method is used for identify such genes.

In the following examples, it is demonstrated how efficiently the method of the invention can be applied to such cellular systems.

EXAMPLE 1

The rat pheochromocytoma PC12 cells were grown (in vitro) in the presence and absence of Nerve Growth Factor (NGF) and epidermal growth factor (EGF) under growth conditions described elsewhere (Saltiel et al. 1996).

The total RNA was isolated using the standard single-step method by Chomczynski and Sacchi according to Sambrook et al 1989.

Total RNA concentration was determined spectrophotometrically and then adjusted to 0.2 $\mu g/\mu l$. This RNA was used directly in the Northern analysis.

For DODET 4×0.5 $\mu g$ total RNA was reverse transcribed in separated pools using the primer 5'-$T_{25}$AA-3'. The same procedure was performed using the 5'-$T_{25}$GC-3' poly-dT anchored primers, giving a total of 2×4×0.5 $\mu g$ of RNA.

First strand synthesis 20.0 $\mu l$ total RNA amount between 0.3 to 1.0 $\mu g$ RNA 3.0 $\mu l$ 5'-$T_{25}$AA-3' Conc. 100 ng/$\mu l$ or 5'-$T_{25}$GC-3' Conc. 100 ng/$\mu l$ 5.0 $\mu l$ 10×cDNA buffer (buffer B from Epicentre Technologies # R19250)

2.0 $\mu l$ dNTPs (25 mM from Pharmacia Biotech)

1.0 kl SuperScript II RT (200 U/$\mu l$) (Gibco BRL # 18064-014)

5.0Retrotherm RT (1 U/$\mu l$) (Epicentre Technologies #R19250)

14.0 $\mu l$ H$_2$O

To obtain high specificity, the cDNA reaction was incubated at 50° C. for 30 minutes followed by 1 hour incubation at 70° C.

Second strand synthesis:

To the first strand reaction, add the following components 15.0 $\mu l$ 10×cDNA buffer 3.0 $\mu l$ Hybridase Thermostable RNase (1 U/$\mu l$) (Epicentre Technologies #H39050)

1.0 $\mu l$ rBst thermostable DNA polymerase (1 U/$\mu l$)) (Epicentre Technologies #BH1100)

81.0 $\mu l$ H$_2$ O

Incubate at 65° C. for 1 hour.

The resulting double stranded cDNA was phenol extracted and precipitated and resuspended in 20 $\mu l$ of H$_2$O. Half of this volume was checked on gel; if a smear between 100 bp and 3000 bp was observed, the rest of the cDNA was used for DODET template production. The resulting cDNAs were digested with 10 U of each of the thermostable restriction enzymes TaqI and BclI at 50° C. for 2 hours. To this mixture, DODET adapters were added and ligated to the ends of the restriction fragments with T$_4$ DNA ligase (1U) resulting in the primary template. 8–15 cycles of nonradioactive pre-amplification, using primers complementary to the DODET adapters, were performed on a small aliquot (1/10th volume) of the primary template (94° C. denaturation; 30 s, 56° C. annealing; 30 s, 72° C. polymerisation; 1 min). The products of the amplification (termed secondary template) were also checked on a 1.5%. agarose gel. As expected, fragment sizes were predominantly between 100 bp and 1000 bp. All amplification reactions were carried out on a PE-9600 thermocycler using Taq DNA-polymerase, both from Perkin Elmer Corp. (Norwalk, Conn., USA). The final template was then diluted 10 fold with $H_2O$.

The adapters ligated to the restriction fragments, the pre-amplification and active PCR are given below:

TaqI adapter SEQ ID NOS: 35 and 36:
5'-CAGCATGAGTCCTGAC
TACTCAGGACTGGC-5'
TaqI pre-amplification primer SEQ ID NO: 37:
5'-CAGCATGAGTCCTGACCGA
TaqI amplification primer SEQ ID NO: 38:
5'-CATGAGTCCTGACCGAN
(N=A or C or G or T)
BclI adapter SEQ ID NOS: 39 and 40:
5'-CTCGTAGACTGCGTACC
CTGACGCATGGCTAG-5'
BclI pre-amplification primer SEQ ID NO: 41:
5'-CTCGTAGACTGCGTACCGATCA
BclI amplification primer SEQ ID NO: 42:
5'-GACTGCGTACCGATCAN
(N=A or C or G or T)

For PCR all the different combinations of one extension (denoted as N above) were available, giving a total of $4^2$ primer combinations. All oligonucleotides were obtained from DNA Technology (Aarhus, Denmark).

Radioactive labelling of the BclI primer was performed using 1U of $T_4$ polynucleotide kinase. Thermocycling was carried out essentially as described above but with 35 cycles and including an 11 cycle touch-down (the annealing temperature was reduced from 65° C. to 56° C. in 0.7° C. steps for 11 cycles and subsequently maintained at 56° C. for 23 cycles). Samples were then boiled after the addition of dye and 50% formamide and separated on a 5% polyacrylamide sequencing type gel (GIBCO BRL Life Technologies Inc., Gaithersburg, Md., USA). All gels were run at standard conditions, such that the 70 bp marker was 3 cm from the bottom of the gel, giving good resolution between 70–800 bp. Gels were then dried directly onto Whatman 3M paper on a slab gel dryer. Labelled DNA fragments were visualised by autoradiography. Gels and films were positionally marked prior to development. The 1 base selective extensions were chosen empirically to yield approximately 50 radioactively labelled fragments per lane.

Bands, identified on the autoradiogram as interesting, were lined up with markings on the film and the dehydrated gel and were excised. Excised fragments were monitored for activity. The gel fragments were isolated using GENECLEAN (BIO101, Califormia USA). DNA was then recovered according to the manufacturer's recommendations. DNA fragments could then be reamplified using the same PCR conditions and primers as used in the initial PCR; however, 15 cycles generally yielded sufficient product for cloning. Cloning was achieved using unpurified PCR product and the vector display-pl23T (Display Systems Biotech, USA). Conditions were used as recommended by the manufacturer.

EXAMPLE 2

Figure 3:
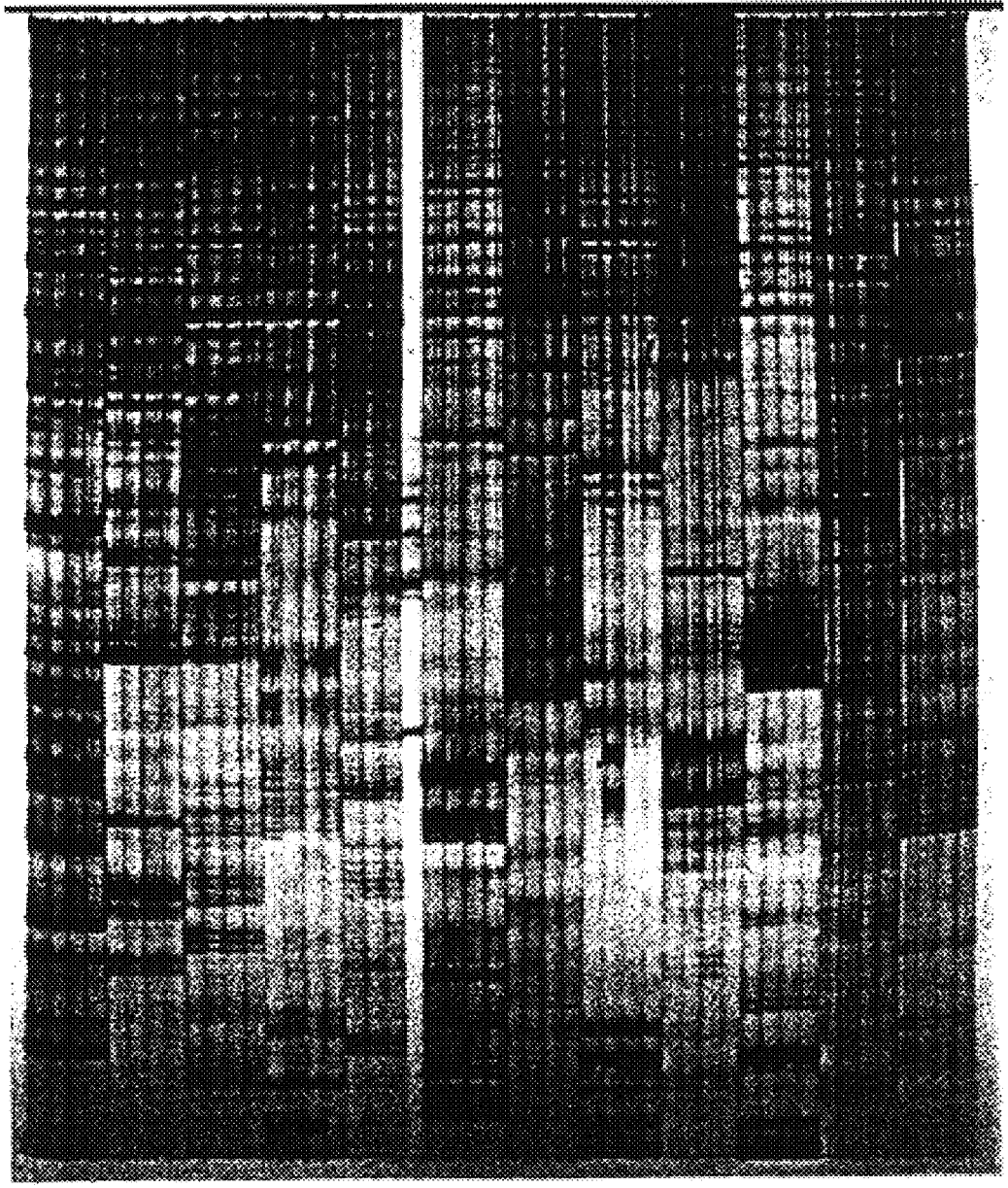

FIG. 3 shows a typical DODET gel produced by amplification of template derived from treatment of PC12 cells with NGF or EGF.

Total RNA was reverse transcribed with the 5'-$T_{25}$AA-3' and $T_{25}$GC-3' poly-dT anchored primers, and after anchor ligation pre-amplification with BclI and TaqI pre-amplification primer pairs was performed.

6 out of 16 possible primer combinations are shown, using 1 selective base, at each restriction enzyme site (FIG. 3). The largest visible products (FIG. 3) are approximately 1000 bp in size and the lower end of the gel corresponds to approximate 100 bp. In this size window an average of 50 bands can be scored for each primer combination. In FIG. 3, various expression patterns can be detected.

Due primarily to the stringent conditions possible in DODET, resolution of the banding pattern is high while the level of background remains at acceptable levels (FIG. 3). Furthermore, quite radical changes in the intensity of individual bands over the treatment period do not seem to affect the patterns of other bands in the same lane.

It is, therefore, possible to conclude that the PCR remains proportionally independent on the concentration of individual substrates in the reaction.

The use of an optimised combination of standard protocols described above for isolating, re-amplifying and cloning individual RDFs, has allowed the identification of a number of transcripts associated with differentiation and proliferation events.

Four RDFs were isolated for further analysis, FIG. 3, bands a, b, c and d.

Sequence analysis revealed that RDF a=RDF b and RDF c=RDF d, as illustrated in FIG. 3.

In all cases appropriate terminal sequences with the correct 1 selective base extensions used in the PCR could be retrieved, demonstrating the stringency and fidelity of the system (data not shown).

EXAMPLE 3

During scanning of the PC12 cellular systems treated with NGF or EGF with different primer combinations, two RDFs (designated RDF01 and RDF02) exhibiting a differential expression during the NGF treatment were isolated (RDF01=RDF a=RDF b and RDF02=RDFc=RDF d. in FIG. 3).

After re-amplification, sub-cloning and DNA sequencing, further DNA analysis revealed two unknown RDFs upregulated after 60 minutes NGF treatment or 90 minutes EGF treatment in the PC12 cellular system. The nucleotide sequences of both RDF01 and RDF02 show less than 10% homology to any existing gene in the GeneBank or EMBL databases.

The expression of RDF01 and RDF02 was further analyzed using Northern blot (FIGS. 4a–4d). Here, transcripts could clearly be detected at 60 minutes NGF treatment or 90 minutes EGF treatment of the PC12 cells, confirming the results obtained using the DODET method, as illustrated in FIG. 3.

Experiments to clone the full length of RDF01 and RDF02, and biological characterisation of their involvement in the differentiation and proliferation, of the PC12 cellular system are currently under investigation.

EXAMPLE 4

Searching for genes modulated by a growth factor.

A human cell line was treated with a growth factor and RNA was isolated a various time points as indicated below.
1 Cell without any treatment (lanes 2, 7, 12, 17, 22)

2 Cell treated with helper agent, 1 day (lanes 3, 8, 13, 18, 23)
3 Cell treated with helper agent and growth factor, 1 day (lanes 4, 9, 14, 19, 24)
4 Cell treated with helper agent, 6 days (lanes 5, 10, 15, 20, 25)
5 Cell treated with helper agent and growth factor, 6 days (lanes 6, 11, 16, 21, 26)

Figure 5:
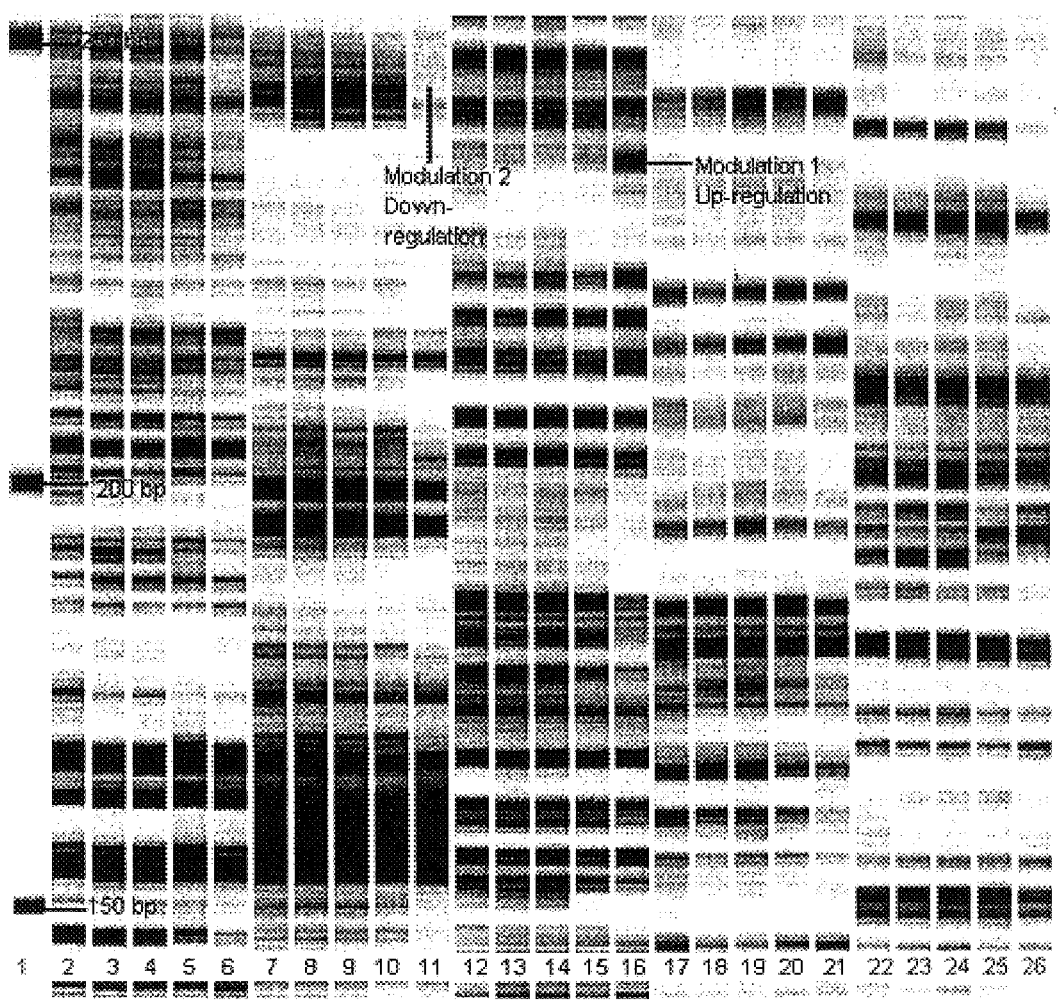

Human RNA was isolated and the gene discovery analysis was performed essentially as described in the legend to FIG. 3. 5 out of 64 amplification primers are shown in FIG. 5, each covering a certain portion of the mRNA pool in the human cell line. The expression analysis was performed on an ALFexpress, an automated fragment analyzer from Pharmacia Biotech, using a Cy5 label.

In lane 11 a downregulation is observed after 6 days of treatment. In lane 16 an upregulation is observed after 6 days of treatment. Both modulations are due to the growth factor, since regulation is only observed with the active growth factor present.

EXAMPLE 5

Searching for genes involved in bacterial resistance to antibiotics.

A *Listeria monocylogia* strain was treated with the Bacteriamycin, Inosin. RNA from a strain resistant to Inosin was further investigated.

1. Bacterial clone 1 without any treatment (lanes 2, 6, 10, 14, 18)
2. Bacterial clone 2 without any treatment (lanes 3, 7, 11, 15, 19)
3. Bacterial clone 3 resistant to Inosin (lanes 4, 8, 12, 16, 20)
4. Bacterial clone 4 resistant to Inosin (lanes 5, 9, 13, 17, 21)

Bacterial RNA was isolated by standard techniques and the gene discovery analysis was performed according to Example 4 and FIG. 5, with the exception that a 5'-NNNNNNYYA primer was used for first strand synthesis.

Figure 6:
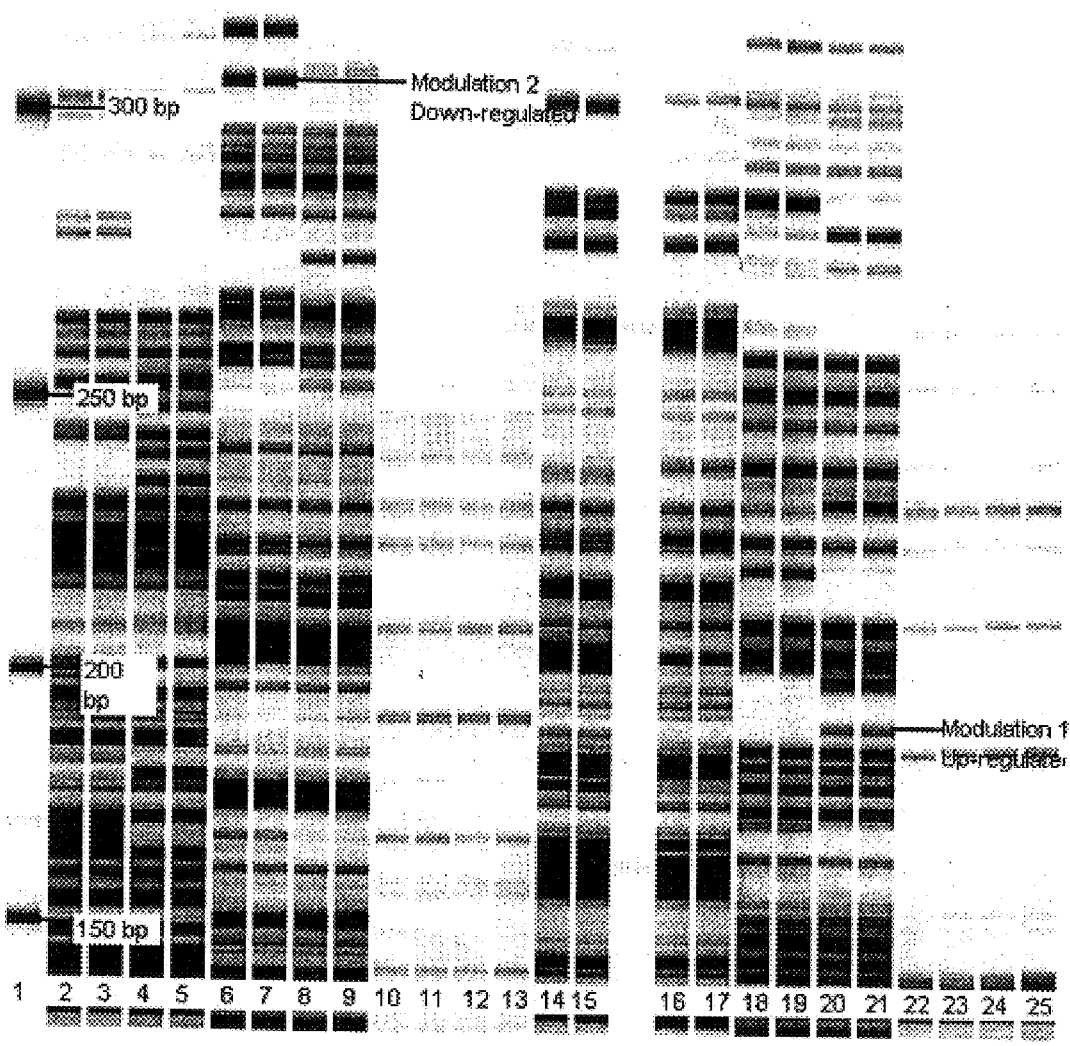

6 of 64 amplification primers are shown in FIG. 6, each covering a certain portion of the mRNA pool in the prokaryotic cell system. The expression analysis was performed on an ALFexpress, an automated fragment analyzer from Pharmacia Biotech, using a Cy5 label.

In lanes 8 and 9 a downregulation is observed and in lanes 20 and 21 an upregulation is observed. Both gene modulations are potential genes involved in the resistance to Inosin.

What is claimed is:

1. A method for preparing a normalized sub-divided library of amplified cDNA fragments from the coding region of mRNAs contained in a sample, the method comprising the steps of
   a) subjecting said mRNA population to reverse transcription using at least one cDNA primer, thereby obtaining first strand cDNA fragments,
   b) synthesizing second strand cDNA complementary to the first strand cDNA fragments by use of the first strand DNA fragments as templates, thereby obtaining double stranded cDNA fragments,
   c) digesting the double stranded cDNA fragments with at least one restriction endonuclease, said endonuclease leaving protruding sticky ends of similar size at the termini of the DNA after digestion, thereby obtaining cleaved cDNA fragments,
   d) adding at least two adapter fragments containing known sequences to the cleaved cDNA fragments obtained in step c), said at least two adapter fragments being able to bind specifically to the sticky ends of the double stranded cDNA produced in step c), the one adapter fragment being able to anneal to the primer having formula II in step f), the second adapter fragment being a termination fragment introducing a block against DNA polymerization in the 5'→3' direction setting out from said termination fragment and said termination fragment being unable to anneal to any primer of the at least two primer sets in step f) during the molecular amplification procedure, the at least two adapter fragments being ligated to the cleaved cDNA fragments obtained in step c) so as to obtain ligated cDNA fragments,
   e) sub-dividing the ligated cDNA fragments obtained in step d) into $4^{n1}$ pools where $1 \leq n1 < 4$, and
   f) subjecting each pool of ligated cDNA fragments obtained in step e) to a molecular amplification procedure so as to obtain amplified cDNA fragments, wherein is used, for an adapter fragment used in step d), a set of amplification primers having the general formula II $$5'\text{-Com-}N_{n1}\text{-}3' \qquad\qquad II$$

wherein Com is a sequence complementary to at least the 5'-end of an adapter fragment which is ligated to the 3'-end of a cleaved cDNA fragment, N is A, G, T, or C, the one primer having the general formula II where n1=0, and the second primer having the general formula II where $1 \leq n1 \leq 4$, said second primer being capable of priming amplification of any nucleotide sequence ligated in its 3'-end to the adapter fragment complementary in its 5'-end to Com.

2. A method according to claim 1, wherein the mRNA is of eukaryotic, Archae or prokaryotic origin.

3. A method according to claim 1, wherein the reverse transcription is carried out in two subsequent steps, the first step comprising carrying out reverse transcription at a temperature in the range from about 25° C. to about 55° C. with an enzyme having reverse transcriptase activity at that temperature, and the second step comprising carrying out reverse transcription at a temperature in the range from about 45° C. to about 95° C. with an enzyme having reverse transcriptase activity at that temperature.

4. A method according to claim 3, wherein reverse transcription in the two steps is effected by non-identical enzymes having reverse transcriptase activity.

5. A method according to claim 4, wherein the non-identical enzymes are added separately in each step or are present in both steps.

6. A method according to claim 5, wherein the activity of the enzyme which is active in the first step is substantially abolished in the second step.

7. A method according to claim 1, wherein step b) is carried out under conditions which minimize the formation of mismatches between nucleotides in the first and second cDNA strands.

8. A method according to claim 1, wherein n1=3 in the second set of amplification primers of formula II.

9. A method according to claim 1, wherein the set of amplification primers having n1=0 in formula II is labelled.

10. A method according to claim 1, wherein the set of amplification primers having formula II wherein $1 \leq n1 \leq 4$ comprises all possible combinations and permutations of A, G, T and C in the group $N_{n1}$.

11. A method according to claim 1, which comprises the further step of separating amplified fragments obtained from the molecular amplification procedure of step f).

12. A method according to claim 11, wherein the separation is performed by gel electrophoresis or chromatography.

13. A method according to claim 11, which further comprises the step of identifying separated amplified fragments.

14. A method according to claim 13, wherein the identification is performed by visualization.

15. A method according to claim 11, wherein labelled nucleotides are visualized, the labelled nucleotides being part of a probe or a part of the amplified fragments.

16. A method according to claim 9, which comprises the further step of separating amplified fragments obtained from the molecular amplification of step f), wherein labelled nucleotides are visualized, and the labelled nucleotides include the labelled amplification primers.

17. A method according to claim 16, wherein the visualization is performed by incorporating radioactive or fluorescent alpha dNTP into the cDNA fragment during PCR, where N=A, C, T, U or G.

18. A method according to claim 1, wherein the restriction endonuclease of step c) is a rare 4 base cutter, said rare 4 base cutter being chosen so as to cleave each complete cDNA into an average of about 3 fragments.

19. A method according to claim 18, wherein the rare 4 base cutter is selected form the group consisting of AciI, AluI, BfaI, BstUI, Csp6I, DpnI, DpnII, HaeIII, HhaI, HinPlI, HpaII, MboI, MnlI, MseI, MspI, NlaIII, RsaI, Sau3AI, TaiI, TaqI, and Tsp509I.

20. A method according to claim 1, wherein the termination fragment in step d) comprises or is a chemically modified nucleotide sequence, said modified nucleotide sequence being a dideoxynucleotide covalently attached to the 3'-end of the nucleotide strand.

21. A method according to claim 3, wherein the reverse transcription in the first step is performed by a reverse transcriptase selected from group of reverse transcriptases from AMV (Avian Myeloblastosis Virus), M-MuLV (murine M-MuLV pol gene), or HIV-1 (HIV virus).

22. A method according to claim 3, wherein the reverse transcription in the second step is performed by a DNA polymerase with reverse transcriptase activity from thermophilic eubacteria, selected from the group of Taq (*Thermus aquaticus*), Stoffel (*Thermus aquaticus*), Tth (*Thermus thermophilus*), Tfl/Tub (*Thermus flavus*), Tru (*Thermus Ruber*), Tca (*Thermus caldophilus*), Tfil (*Thermus filiformis*), Tbr (*Thermus Brockianus*), Bst (*B. Stearothermophilus*), Bca (*B. Caldotenax* YT-G), Bcav (*B. Caldovelox* YT-F), FjSS3-B.1 (Thermotoga FjSS3-B.1), Tma (*Thermus Maritima*), UITma (*T. Maritima*), Tli (*T. Litoralis*), Tli exo- (*T. Litoralis*), 9° N-7 (Thermococcus sp.), BG-D (Pyrococcus sp.), Pfu (*P. furiosus*), Pwo (*P. woesei*), Sac (*S. Acidocaldarius*), SsoI (*S. Solfataricus*), Tac (*T. Acidophilum*), and Mth (*Methananococcus voltae*).

23. A method according to claim 3, wherein the enzyme effecting reverse transcription in the second step is Tth or Taq.

* * * * *

UNITED STATES PATENT AND TRADEMARK OFFICE
CERTIFICATE OF CORRECTION

PATENT NO. : 6,261,770 B1
DATED : July 17, 2001
INVENTOR(S) : Peter Rolf Warthoe It is certified that error appears in the above-identified patent and that said Letters Patent is hereby corrected as shown below:

<u>Title page,</u>
Related U.S. Application Data, insert -- U.S. Application Serial No. 08/871,030 dated May 19, 1997 --.

<u>Column 35,</u>
Line 46, item e, change "$1 \leq n1 < 4$" to -- $1 \leq n1 \leq 4$ --;
Line 55, change "wherein Corn" to -- wherein Com --; and <u>Column 38,</u>
Line 10, change "selected form" to -- selected from --.

Signed and Sealed this

Twenty-first Day of May, 2002

Attest:

JAMES E. ROGAN
Attesting Officer
Director of the United States Patent and Trademark Office

SEQUENCE LISTING

```
<160> NUMBER OF SEQ ID NOS: 42

<210> SEQ ID NO: 1
<211> LENGTH: 19
<212> TYPE: DNA
<213> ORGANISM: Thermophilic eubacteria

<400> SEQUENCE: 1
cagcatgagt cctgaccga                                              19

<210> SEQ ID NO: 2
<211> LENGTH: 22
<212> TYPE: DNA
<213> ORGANISM: Thermophilic eubacteria

<400> SEQUENCE: 2
ctcgtagact gcgtaccgat ca                                          22

<210> SEQ ID NO: 3
<211> LENGTH: 17
<212> TYPE: DNA
<213> ORGANISM: Thermophilic eubacteria

<400> SEQUENCE: 3
catgagtcct gaccgaa                                                17

<210> SEQ ID NO: 4
<211> LENGTH: 17
<212> TYPE: DNA
<213> ORGANISM: Thermophilic eubacteria

<400> SEQUENCE: 4
gactgcgtac cgatcaa                                                17

<210> SEQ ID NO: 5
<211> LENGTH: 17
<212> TYPE: DNA
<213> ORGANISM: Thermophilic eubacteria
```

-continued

```
<400> SEQUENCE: 5
catgagtcct gaccgaa                                                17

<210> SEQ ID NO: 6
<211> LENGTH: 17
<212> TYPE: DNA
<213> ORGANISM: Thermophilic eubacteria

<400> SEQUENCE: 6
gactgcgtac cgatcac                                                17

<210> SEQ ID NO: 7
<211> LENGTH: 17
<212> TYPE: DNA
<213> ORGANISM: Thermophilic eubacteria

<400> SEQUENCE: 7
catgagtcct gaccgaa                                                17

<210> SEQ ID NO: 8
<211> LENGTH: 17
<212> TYPE: DNA
<213> ORGANISM: Thermophilic eubacteria

<400> SEQUENCE: 8
gactgcgtac cgatcag                                                17

<210> SEQ ID NO: 9
<211> LENGTH: 17
<212> TYPE: DNA
<213> ORGANISM: Thermophilic eubacteria

<400> SEQUENCE: 9
catgagtcct gaccgaa                                                17

<210> SEQ ID NO :10
<211> LENGTH: 17
<212> TYPE: DNA
<213> ORGANISM: Thermophilic eubacteria

<400> SEQUENCE: 10
gactgcgtac cgatcat                                                17

<210> SEQ ID NO :11
<211> LENGTH: 17
<212> TYPE: DNA
<213> ORGANISM: Thermophilic eubacteria

<400> SEQUENCE: 11
catgagtcct gaccgac                                                17

<210> SEQ ID NO :12
<211> LENGTH: 17
<212> TYPE: DNA
<213> ORGANISM: Thermophilic eubacteria

<400> SEQUENCE: 12
gactgcgtac cgatcaa                                                17

<210> SEQ ID NO :13
<211> LENGTH: 17
<212> TYPE: DNA
<213> ORGANISM: Thermophilic eubacteria
```

```
<400> SEQUENCE: 13
catgagtcct gaccgac                                                    17

<210> SEQ ID NO :14
<211> LENGTH: 17
<212> TYPE: DNA
<213> ORGANISM: Thermophilic eubacteria

<400> SEQUENCE: 14
gactgcgtac cgatcac                                                    17

<210> SEQ ID NO :15
<211> LENGTH: 13
<212> TYPE: DNA
<213> ORGANISM: Thermophilic eubacteria

<400> SEQUENCE: 15
aaaaaaaaaa aaa                                                        13

<210> SEQ ID NO :16
<211> LENGTH: 12
<212> TYPE: DNA
<213> ORGANISM: Thermophilic eubacteria

<400> SEQUENCE: 16
tttttttttt tt                                                         12

<210> SEQ ID NO: 17
<211> LENGTH: 35
<212> TYPE: DNA
<213> ORGANISM: Thermophilic eubacteria
<220> FEATURE:
<221> NAME/KEY: variation
<222> LOCATION: (1)..(35)
<223> OTHER INFORMATION: N can be A or G or T or C

<400> SEQUENCE: 17
nnnntcgann nnnnnnnnnn nnnnnntgat cannn                                35

<210> SEQ ID NO: 18
<211> LENGTH: 35
<212> TYPE: DNA
<213> ORGANISM: Thermophilic eubacteria
<220> FEATURE:
<221> NAME/KEY: variation
<222> LOCATION: (1)..(35)
<223> OTHER INFORMATION: N can be A or G or T or C

<400> SEQUENCE: 18
nnnnagctnn nnnnnnnnnn nnnnnnacta gtnnn                                35

<210> SEQ ID NO: 19
<211> LENGTH: 22
<212> TYPE: DNA
<213> ORGANISM: Thermophilic eubacteria
<220> FEATURE:
<221> NAME/KEY: variation
<222> LOCATION: (1)..(22)
<223> OTHER INFORMATION: N can be A or G ot T or C

<400> SEQUENCE: 19
cgannnnnnn nnnnnnnnnn nt                                              22

<210> SEQ ID NO: 20
<211> LENGTH: 24
```

```
<212> TYPE: DNA
<213> ORGANISM: thermophilic bacterium PS3
<220> FEATURE:
<221> NAME/KEY: variation
<222> LOCATION: (1)..(24)
<223> OTHER INFORMATION: N can be A or G or T or C

<400> SEQUENCE: 20
tnnnnnnnnn nnnnnnnnna ctag                                         24

<210> SEQ ID NO: 21
<211> LENGTH: 61
<212> TYPE: DNA
<213> ORGANISM: Thermophilic eubacteria
<220> FEATURE:
<221> NAME/KEY: variation
<222> LOCATION: (1)..(61)
<223> OTHER INFORMATION: N can be A or G ot T or C
<220> FEATURE:
<221> NAME/KEY: variation
<222> LOCATION: (1)..(61)
<223> OTHER INFORMATION: V can be A or G or C

<400> SEQUENCE: 21
nnnnnnnnnn nnnnnnnnvc gannnnnnnn nnnnnnnnnn ntgatcbnnn nnnnnnnnnn    60 n                                                                   61

<210> SEQ ID NO: 22
<211> LENGTH: 61
<212> TYPE: DNA
<213> ORGANISM: Thermophilic eubacteria
<220> FEATURE:
<221> NAME/KEY: variation
<222> LOCATION: (1)..(61)
<223> OTHER INFORMATION: N can be A or G or T or C
<220> FEATURE:
<221> NAME/KEY: variation
<222> LOCATION: (1)..(61)
<223> OTHER INFORMATION: V can be A or G or C

<400> SEQUENCE: 22
nnnnnnnnnn nnnnnnnbg ctnnnnnnnn nnnnnnnnnn nactagvnnn nnnnnnnnnn     60 n                                                                   61

<210> SEQ ID NO: 23
<211> LENGTH: 64
<212> TYPE: DNA
<213> ORGANISM: Thermophilic eubacteria
<220> FEATURE:
<221> NAME/KEY: variation
<222> LOCATION: (1)..(64)
<223> OTHER INFORMATION: N can be A or G or T or C
<220> FEATURE:
<221> NAME/KEY: variation
<222> LOCATION: (1)..(64)
<223> OTHER INFORMATION: V can be A or G or C

<400> SEQUENCE: 23
nnnnnnnnnn nnnnnnnnvc gannnnnnnn nnnnnnnnnn ntgatcbnnn nnnnnnnnnn    60 nnnn                                                                64

<210> SEQ ID NO: 24
<211> LENGTH: 64
<212> TYPE: DNA
<213> ORGANISM: Thermophilic eubacteria
<220> FEATURE:
<221> NAME/KEY: variation
<222> LOCATION: (1)..(64)
```

```
<223> OTHER INFORMATION: N can be A or G ot T or C
<220> FEATURE:
<221> NAME/KEY: variation
<222> LOCATION: (1)..(64)
<223> OTHER INFORMATION: V can be A or G or C

<400> SEQUENCE: 24
nnnnnnnnnn nnnnnnnnbg ctnnnnnnnn nnnnnnnnnn nactagvnnn nnnnnnnnnn    60 nnnn                                                                  64

<210> SEQ ID NO: 25
<211> LENGTH: 23
<212> TYPE: DNA
<213> ORGANISM: Thermophilic eubacteria
<220> FEATURE:
<221> NAME/KEY: variation
<222> LOCATION: (1)..(23)
<223> OTHER INFORMATION: N can be A or G or T or C
<220> FEATURE:
<221> NAME/KEY: variation
<222> LOCATION: (1)..(23)
<223> OTHER INFORMATION: V can be A or G or C

<400> SEQUENCE: 25
nnnnnnnnnn nnnnnnnnvc gat                                             23

<210> SEQ ID NO: 26
<211> LENGTH: 23
<212> TYPE: DNA
<213> ORGANISM: Thermophilic eubacteria
<220> FEATURE:
<221> NAME/KEY: variation
<222> LOCATION: (1)..(23)
<223> OTHER INFORMATION: N can be A or G or T or C
<220> FEATURE:
<221> NAME/KEY: variation
<222> LOCATION: (1)..(23)
<223> OTHER INFORMATION: V can be A or G or C

<400> SEQUENCE: 26
nnnnnnnnnn nnnnnnnnvc gag                                             23

<210> SEQ ID NO: 27
<211> LENGTH: 23
<212> TYPE: DNA
<213> ORGANISM: Thermophilic eubacteria
<220> FEATURE:
<221> NAME/KEY: variation
<222> LOCATION: (1)..(23)
<223> OTHER INFORMATION: N can be A or G or T or C
<220> FEATURE:
<221> NAME/KEY: variation
<222> LOCATION: (1)..(23)
<223> OTHER INFORMATION: V can be A or G or C

<400> SEQUENCE: 27
nnnnnnnnnn nnnnnnnnvc gac                                             23

<210> SEQ ID NO: 28
<211> LENGTH: 23
<212> TYPE: DNA
<213> ORGANISM: Thermophilic eubacteria
<220> FEATURE:
<221> NAME/KEY: variation
<222> LOCATION: (1)..(23)
<223> OTHER INFORMATION: N can be A or G or T or C
<220> FEATURE:
<221> NAME/KEY: variation
<222> LOCATION: (1)..(23)
<223> OTHER INFORMATION: V can be A or G or C
```

```
<400> SEQUENCE: 28
nnnnnnnnnn nnnnnnnnvc gaa                                               23

<210> SEQ ID NO: 29
<211> LENGTH: 63
<212> TYPE: DNA
<213> ORGANISM: Thermophilic eubacteria
<220> FEATURE:
<221> NAME/KEY: variation
<222> LOCATION: (1)..(63)
<223> OTHER INFORMATION: N can be A or G or T or C
<220> FEATURE:
<221> NAME/KEY: variation
<222> LOCATION: (1)..(63)
<223> OTHER INFORMATION: V can be A or G or C

<400> SEQUENCE: 29
nnnnnnnnnn nnnnnnnnvc gannnnnnnn nnnnnnnnnn tgatcbnnnn nnnnnnnnnn      60 nnn                                                                     63

<210> SEQ ID NO: 30
<211> LENGTH: 63
<212> TYPE: DNA
<213> ORGANISM: Thermophilic eubacteria
<220> FEATURE:
<221> NAME/KEY: variation
<222> LOCATION: (1)..(63)
<223> OTHER INFORMATION: N can be A or G or T or C
<220> FEATURE:
<221> NAME/KEY: variation
<222> LOCATION: (1)..(63)
<223> OTHER INFORMATION: V can be A or G or C

<400> SEQUENCE: 30
nnnnnnnnnn nnnnnnnbg ctnnnnnnnn nnnnnnnnnn actagvnnnn nnnnnnnnnn       60 nnn                                                                     63

<210> SEQ ID NO: 31
<211> LENGTH: 23
<212> TYPE: DNA
<213> ORGANISM: Thermophilic eubacteria
<220> FEATURE:
<221> NAME/KEY: variation
<222> LOCATION: (1)..(23)
<223> OTHER INFORMATION: N can be A or G or T or C
<220> FEATURE:
<221> NAME/KEY: variation
<222> LOCATION: (1)..(23)
<223> OTHER INFORMATION: V can be A or G or C

<400> SEQUENCE: 31
aactagvnnn nnnnnnnnnn nnn                                               23

<210> SEQ ID NO: 32
<211> LENGTH: 23
<212> TYPE: DNA
<213> ORGANISM: Thermophilic eubacteria
<220> FEATURE:
<221> NAME/KEY: variation
<222> LOCATION: (1)..(23)
<223> OTHER INFORMATION: N can be A or G or T or C
<220> FEATURE:
<221> NAME/KEY: variation
<222> LOCATION: (1)..(23)
<223> OTHER INFORMATION: V can be A or G or C

<400> SEQUENCE: 32
cactagvnnn nnnnnnnnnn nnn                                               23
```

```
<210> SEQ ID NO: 33
<211> LENGTH: 23
<212> TYPE: DNA
<213> ORGANISM: Thermophilic eubacteria
<220> FEATURE:
<221> NAME/KEY: variation
<222> LOCATION: (1)..(23)
<223> OTHER INFORMATION: N can be A or G or T or C
<220> FEATURE:
<221> NAME/KEY: variation
<222> LOCATION: (1)..(23)
<223> OTHER INFORMATION: V can be A or G or C

<400> SEQUENCE: 33
gactagvnnn nnnnnnnnnn nnn                                    23

<210> SEQ ID NO: 34
<211> LENGTH: 23
<212> TYPE: DNA
<213> ORGANISM: Thermophilic eubacteria
<220> FEATURE:
<221> NAME/KEY: variation
<222> LOCATION: (1)..(23)
<223> OTHER INFORMATION: N can be A or G or T or C
<220> FEATURE:
<221> NAME/KEY: variation
<222> LOCATION: (1)..(23)
<223> OTHER INFORMATION: V can be A or G or C

<400> SEQUENCE: 34
tactagvnnn nnnnnnnnnn nnn                                    23

<210> SEQ ID NO: 35
<211> LENGTH: 16
<212> TYPE: DNA
<213> ORGANISM: Thermophilic eubacteria

<400> SEQUENCE: 35
cagcatgagt cctgac                                            16

<210> SEQ ID NO: 36
<211> LENGTH: 14
<212> TYPE: DNA
<213> ORGANISM: Thermophilic eubacteria

<400> SEQUENCE: 36
tactcaggac tggc                                              14

<210> SEQ ID NO: 37
<211> LENGTH: 19
<212> TYPE: DNA
<213> ORGANISM: Thermophilic eubacteria

<400> SEQUENCE: 37
cagcatgagt cctgaccga                                         19

<210> SEQ ID NO: 38
<211> LENGTH: 17
<212> TYPE: DNA
<213> ORGANISM: Thermophilic eubacteria
<220> FEATURE:
<221> NAME/KEY: variation
<222> LOCATION: (1)..(17)
<223> OTHER INFORMATION: N can be A or C or G or T

<400> SEQUENCE: 38
catgagtcct gaccgan                                           17
```

-continued

```
<210> SEQ ID NO: 39
<211> LENGTH: 17
<212> TYPE: DNA
<213> ORGANISM: Thermophilic eubacteria

<400> SEQUENCE: 39
ctcgtagact gcgtacc                                                 17

<210> SEQ ID NO: 40
<211> LENGTH: 15
<212> TYPE: DNA
<213> ORGANISM: Thermophilic eubacteria

<400> SEQUENCE: 40
ctgacgcatg gctag                                                   15

<210> SEQ ID NO: 41
<211> LENGTH: 22
<212> TYPE: DNA
<213> ORGANISM: Thermophilic eubacteria

<400> SEQUENCE: 41
ctcgtagact gcgtaccgat ca                                           22

<210> SEQ ID NO: 42
<211> LENGTH: 17
<212> TYPE: DNA
<213> ORGANISM: Thermophilic eubacteria
<220> FEATURE:
<221> NAME/KEY: unsure
<222> LOCATION: (1)..(17)
<223> OTHER INFORMATION: N can be A or C or G or T

<400> SEQUENCE: 42
gactgcgtac cgatcan                                                 17
```